(12) United States Patent
List

(10) Patent No.: US 12,042,145 B2
(45) Date of Patent: Jul. 23, 2024

(54) INSERTION DEVICE AND METHOD FOR INSERTING A MEDICAL DEVICE

(71) Applicant: Roche Diabetes Care, Inc., Indianapolis, IN (US)

(72) Inventor: Hans List, Oberzent (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 18/189,821

(22) Filed: Mar. 24, 2023

(65) Prior Publication Data

US 2023/0225728 A1 Jul. 20, 2023

Related U.S. Application Data

(63) Continuation of application No. PCT/EP2021/076137, filed on Sep. 23, 2021.

(30) Foreign Application Priority Data

Sep. 25, 2020 (EP) .................................... 20198479

(51) Int. Cl.
*A61B 17/068* (2006.01)
*A61B 17/29* (2006.01)

(52) U.S. Cl.
CPC .... *A61B 17/068* (2013.01); *A61B 2017/2933* (2013.01); *A61B 2017/2946* (2013.01)

(58) Field of Classification Search
None
See application file for complete search history.

(56) References Cited

U.S. PATENT DOCUMENTS 7,310,544 B2 12/2007 Brister et al.
7,699,807 B2 * 4/2010 Faust ................. A61B 5/14503
604/157

(Continued)

FOREIGN PATENT DOCUMENTS

EP 1 624 914 A1 2/2006
EP 3 542 712 A1 9/2019

(Continued)

OTHER PUBLICATIONS

International Search Report and Written Opinion of the International Searching Authority, PCT/EP2021/076137, Jan. 4, 2022, 14 pages.

*Primary Examiner* — Nathaniel C Chukwurah
(74) *Attorney, Agent, or Firm* — Bose McKinney & Evans LLP

(57) ABSTRACT

An insertion device includes an insertion component that inserts a medical device into body tissue of a user. The insertion device also includes an insertion component retractor, a cap, a guide sleeve having a ramp, an insertion sleeve and an elastic member. For inserting the medical device, the cap, the insertion component retractor and the insertion sleeve are movable relative to the guide sleeve from a distal position to a proximal position. The ramp twists the insertion component retractor relative to the guide sleeve and the insertion sleeve when the cap is moved from its distal position to its proximal position. The cap is movable from its proximal position to its distal position and the insertion component retractor is thereby moved from its proximal position to its distal position. An associated method of using the insertion device is also disclosed.

16 Claims, 14 Drawing Sheets

(56) References Cited

U.S. PATENT DOCUMENTS

| | | | |
|---|---|---|---|
| 2010/0286714 | A1 | 11/2010 | Gyrn et al. |
| 2013/0150691 | A1* | 6/2013 | Pace ............... A61B 5/150358 |
| | | | 600/347 |
| 2013/0245604 | A1 | 9/2013 | Kouyoumjian et al. |
| 2015/0258283 | A1 | 9/2015 | Imai et al. |
| 2016/0331283 | A1* | 11/2016 | Rao ................... A61B 5/14503 |
| 2020/0178899 | A1 | 6/2020 | Chae et al. |

FOREIGN PATENT DOCUMENTS

| | | | |
|---|---|---|---|
| WO | WO 2004/098683 A1 | 11/2004 | |
| WO | WO-2010091005 A1 * | 8/2010 | ........... A61B 5/0004 |

* cited by examiner

INSERTION DEVICE AND METHOD FOR INSERTING A MEDICAL DEVICE

RELATED APPLICATIONS

This application is a continuation of International Patent Application No. PCT/EP2021/076137, filed Sep. 23, 2021, which claims priority to EP 20 198 479.6, filed Sep. 25, 2020, both of which are hereby incorporated herein by reference.

BACKGROUND

This disclosure relates to an insertion device and a method for inserting a medical device into a body tissue of a user. The medical device may specifically be configured for detecting at least one analyte in a body fluid of the user. The insertion device and the method may be applied in the field of continuous monitoring of the analyte in the body fluid of the user, specifically in the field of home care and in the field of professional care, such as in hospitals. Other applications, however, are also feasible.

Monitoring certain body functions, more particularly monitoring one or more analyte concentrations such as one or more metabolite concentration in a body fluid of a user plays an important role in the prevention and treatment of various diseases. Such analytes can include by way of example, but not exclusively, glucose, lactate, cholesterol or other types of analytes and metabolites. Without restricting further possible applications, this disclosure will be described in the following text with reference to glucose monitoring. However, additionally or alternatively, this disclosure can also be applied to other types of analytes, such as the analytes mentioned above.

Generally, systems for long-term monitoring of an analyte in a body tissue of a user as well as corresponding insertion devices are known. For example, U.S. Pat. No. 7,310,544 B2 discloses systems and methods for measuring an analyte in a host. More particularly, this disclosure relates to systems and methods for transcutaneous measurement of glucose in a host.

EP 1 624 914 discloses a device comprising a housing having a mounting surface adapted for application to the skin of a subject, a needle with a pointed end portion adapted to penetrate the skin of the subject, the needle having a first position in which the distal end portion is retracted within the housing, and a second position in which the distal end portion projects relative to the mounting surface. The device further comprises driving means actuatable to cause activation as well as release of the driving means, thereby moving the needle from the first position to the second position. By this arrangement the needle device can be supplied to the user in a non-energized state, the energizing taking place when the device is actuated by the user which means that energy will be stored only for a period from a few seconds to a few hours or days.

Another example of an apparatus for insertion of a medical device such as an analyte sensor is known from EP 3 542 712 A1.

Other insertion devices are known for drug delivery systems. For example, U.S. Publication No. 2013/0245604 A1 describes system including two major components: an auto-injector device containing two medicaments and a medicated module containing at least one medicament. The medicated module interfaces with the auto-injector device such that a combination dose comprising all of the medicaments can be delivered via a single dispense interface of the medicated module.

For monitoring an analyte in a body fluid, a sensor may be brought in contact with the body fluid. Generally, this requires inserting the sensor subcutaneously. There are systems, as an example, in which the sensor may be connected to an electronics unit upon insertion of the sensor. These systems may comprise a sensor base plate through which the sensor is inserted. After insertion of the sensor, the electronics unit may be connected to the base plate and the sensor. The base plate may reveal an exposed spot within the covered area and the sensor may be inserted into the skin of the user at the exposed spot. For systems in which the sensor is fixedly connected to the electronics unit, the insertion of the sensor may be performed simultaneously with the attachment of the electronics unit to the skin of the user.

Generally, the sensor may be inserted using an insertion component, such as a needle. Often such systems comprise a mechanism which retracts the insertion component after the electronics unit was attached to the skin of the user and the sensor was inserted into the skin of the user. The insertion component may be retracted deeply into the housing of the system to minimize the infection risk. The retraction of the insertion component may be initiated mechanically after insertion movement of the insertion component into the skin.

Despite the advantage achieved by the above-mentioned devices, several technical challenges remain. The insertion component has to be retracted close to but still before the deepest point of insertion movement. This may cause the insertion component to be retracted before the sensor has penetrated the skin sufficiently or even at all. The needle may exert a force to the skin in which the sensor shall be inserted. The skin may bulge inward under the attack of this force. In commonly known devices, close to the end of the insertion movement, the insertion needle is retracted. Because of the inward bulging of the skin, the sensor may not fully be inserted when the needle starts to disappear rapidly. The result may be a not or just partly inserted sensor. In this case, the sensor has to penetrate the skin of the user by its own when the insertion component has been retracted. However, in general, the sensor may be soft and flexible in order to minimize irritations in the skin of the user such that the sensor may not be able for piercing and advancing into the skin of the user when the insertion component has retracted without accomplishing a full insertion. This may result in that the sensor may be not fully inserted subcutaneously into the skin of the user and may potentially be bent upon insertion. Thus, the sensor may not be able to perform its function.

SUMMARY

It is therefore desirable to provide a method and an insertion device which at least partially address the above-mentioned technical challenges. An insertion device is disclosed herein which allows a safe and user-friendly handling of the insertion device while ensuring a reliable insertion of a medical device into a body tissue of a user.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once. It shall be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "ramp," "groove," and "edge," to name just a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect of this disclosure, an insertion device for inserting a medical device into a body tissue of a user is disclosed.

The term "medical device" as used herein is a broad term and is to be given its ordinary and customary meaning to a person of ordinary skill in the art and is not to be limited to a special or customized meaning. The term specifically may refer, without limitation, to an arbitrary element or article being configured for use in the field of medical technology, specifically in the field of medical analytics or medical diagnostics. The medical device may be configured for performing at least one medical function and/or for being used in at least one medical process, such as one or more of a therapeutic process, a diagnostic process or another medical process.

For example, the medical device may be or may comprise at least one analyte sensor for detecting at least one analyte in a bodily fluid of a user, such as in a bodily fluid contained in a body tissue of the user. The analyte sensor may be configured for being used in qualitatively and/or quantitatively detecting the at least one analyte. The term "analyte" as used herein is a broad term and is to be given its ordinary and customary meaning to a person of ordinary skill in the art and is not to be limited to a special or customized meaning. The term specifically may refer, without limitation, to a chemical and/or biological substance which takes part in the metabolism of the body of the user. Specifically, the analyte may be a metabolite or a combination of two or more metabolites. As an example, the analyte may be selected from the group consisting of: glucose, lactate, triglycerides, and cholesterol. Still, other analytes or combinations of two or more analytes may be detected. The body tissue specifically may be or may comprise fatty tissue and/or interstitium. Other types of body tissue, however, are feasible.

The term "analyte sensor" as used herein is a broad term and is to be given its ordinary and customary meaning to a person of ordinary skill in the art and is not to be limited to a special or customized meaning. The term specifically may refer, without limitation, to a sensor which is capable of qualitatively or quantitatively detecting the presence and/or the concentration of the at least one analyte.

The analyte sensor may be an electrochemical analyte sensor. The analyte sensor may comprise at least two electrodes. Specifically, the analyte sensor may comprise at least one two-electrode sensor. The two-electrode sensor may comprise precisely two electrodes, such as a working electrode and at least one further electrode such as a counter electrode, in particular a working electrode and a combined counter/reference electrode. The working electrode may comprise a working electrode pad and, optionally, at least one test chemical disposed thereon. The counter electrode may comprise a conductive electrode pad. Additionally and optionally, one or more redox materials may be disposed thereon. The analyte sensor may further comprise one or more leads for electrically contacting the electrodes. The leads may, during insertion or at a later point in time, be connected to an electronics unit, such as one or more measurement devices adapted for measuring electrical currents and/or electrical voltages, such as to one or more potentiostats. Preferably, the leads already connected to the electronics unit before insertion of the analyte sensor.

Specifically, the analyte sensor may be a strip-shaped analyte sensor having a flexible substrate and the electrodes disposed thereon. As an example, the analyte sensor may have a total length of 5 mm to 50 mm, specifically a total length of 7 mm to 30 mm. The term "total length" within the context of this disclosure relates to the overall length of the analyte sensor which means the portion of the analyte sensor which is inserted and the portion of the analyte sensor which is connected to the electronics unit. The portion of the analyte sensor which is inserted is also called the in-vivo portion, the portion of the analyte sensor which is connected to the electronics unit is also called the ex vivo portion. Preferably, the in vivo portion has a length in the range from 3 mm to 12 mm.

The analyte sensor may further comprise a biocompatible cover, such as a biocompatible membrane which fully or partially covers the analyte sensor and which prevents the test chemical from migrating into the body tissue and which allows for a diffusion of the bodily fluid and/or the analyte to the electrodes.

Other embodiments of electrochemical analyte sensors, such as three-electrode sensors, may be feasible. For example, the three-electrode sensor may comprise, in addition to the working electrode and the counter electrode, a reference electrode.

In another embodiment, the analyte sensor may be an optical analyte sensor. For example, the analyte sensor may comprise a flexible light guide with glucose sensitive coating at its end and/or a tube like carrier with functional elements at inner or outer walls. Other embodiments of the analyte sensor may be possible too. For potential embodiments of analyte sensors, reference may be made to the above-mentioned prior art documents.

For example, the medical device may be or may comprise at least one infusion cannula. The term "infusion cannula" as used herein is a broad term and is to be given its ordinary and customary meaning to a person of ordinary skill in the art and is not to be limited to a special or customized meaning. The term specifically may refer, without limitation, to a hollow tube configured for delivering and/or infusing a medication into the body tissue of the user, in particular for delivering and/or infusing insulin into the body tissue of the user.

The term "user" as used herein is a broad term and is to be given its ordinary and customary meaning to a person of ordinary skill in the art and is not to be limited to a special or customized meaning. The term specifically relates to a person intending to monitor an analyte value, such as a glucose value, in the person's body tissue and/or to deliver medication, such as insulin, into the person's body tissue. In an embodiment, the term specifically may refer, without limitation, to a person using the insertion device. However, in an embodiment, the person using the insertion device is different from the user. For example, the medical device may be inserted by a person different from the user into the user's body tissue. For example, the user may be a patient suffering from a disease, such as diabetes.

The term "inserting" as used herein is a broad term and is to be given its ordinary and customary meaning to a person of ordinary skill in the art and is not to be limited to a special or customized meaning. The term specifically may refer, without limitation, to an action or process of one or more of transcutaneously or subcutaneously implanting and/or positioning the medical device into the body tissue of the user. The medical device, such as the analyte sensor, may fully or partially be inserted into the body tissue. The insertion of the medical device may be performed by using the insertion device. After insertion, the medical device or at least a part of the medical device may remain in the body tissue of the user for a predetermined period of time, such as for several hours, specifically for one or more days, more specifically for up to one week, even more specifically for up to two weeks or even more. The medical device may be configured for continuously monitoring and/or detecting the analyte in the body fluid of the user.

The term "insertion device" as used herein is a broad term and is to be given its ordinary and customary meaning to a person of ordinary skill in the art and is not to be limited to a special or customized meaning. The term specifically may refer, without limitation, to a device configured for inserting the medical device into the body tissue. The insertion device may be configured for transcutaneously or subcutaneously inserting the medical device into the body tissue, such as by performing an incision or a puncture in a skin of the user and by transferring the medical device fully or partially into the body tissue.

The insertion device comprises:
i) the medical device;
ii) an insertion component configured for inserting the medical device into the body tissue;
iii) an insertion component retractor;
iv) a cap;
v) a guide sleeve comprising at least one ramp;
vi) an insertion sleeve; and
vii) an elastic member.

For inserting the medical device, the cap, the insertion component retractor and the insertion sleeve are movable relative to the guide sleeve from a distal position to a proximal position. The ramp of the guide sleeve is configured to twist the insertion component retractor relative to the guide sleeve and the insertion sleeve when the cap is moved from its distal position to its proximal position. The cap is movable from its proximal position to its distal position, thereby the insertion component retractor is moved from its proximal position to its distal position.

The term "insertion component" as used herein is a broad term and is to be given its ordinary and customary meaning to a person of ordinary skill in the art and is not to be limited to a special or customized meaning. The term specifically may refer, without limitation, to an arbitrary element which may be insertable at least partially into the body tissue, particularly in order to deliver or to transfer a further element. The insertion component may be configured for supporting the insertion of the medical device. The insertion component may comprise a tip or a sharp end for inserting the medical device into the body tissue. The insertion component may be or may comprise an insertion cannula or an insertion needle. The term "insertion cannula" as used herein is a broad term and is to be given its ordinary and customary meaning to a person of ordinary skill in the art and is not to be limited to a special or customized meaning. The term specifically may refer, without limitation, to a hollow needle which may be at least partially slotted. The medical device may be received within the insertion cannula, such as within a lumen of the insertion cannula. The term "insertion needle" as used herein is a broad term and is to be given its ordinary and customary meaning to a person of ordinary skill in the art and is not to be limited to a special or customized meaning. The term specifically may refer, without limitation, to a compact needle, specifically without a slot and without any hollow parts. The medical device may be received on an outer surface of the insertion needle.

After insertion, the medical device may remain in the body tissue of the user. The insertion component, however, may be retracted from the body tissue of the user into the insertion device after inserting the medical device. For retracting the insertion component the insertion device may comprise the insertion component retractor.

The term "insertion component retractor" as used herein is a broad term and is to be given its ordinary and customary meaning to a person of ordinary skill in the art and is not to be limited to a special or customized meaning. The term specifically may refer, without limitation, to at least one element of the insertion device configured for retracting the insertion component. The insertion component retractor may be configured for suspending the insertion component during insertion movement and pull it out from the skin of the user during retraction movement.

An engagement between the insertion component retractor and the insertion component may be loose. The engagement between the insertion component retractor and the insertion component may be established during a production process. The insertion component retractor may comprise at least one finger, gripper, hook, pincer or the like configured for retracting the insertion component. The finger, gripper, hook, pincer or the like may be arranged at a proximal end of the insertion component retractor, wherein, when the insertion device is in use, the proximal end of the insertion component retractor may point towards the body tissue of the user. For example, the insertion component retractor may comprise two or more fingers, grippers, hooks or pincers arranged symmetrically around the insertion component. For example, the insertion device may comprise at least one plunger or pull rod connected to the insertion component. The insertion component retractor may be connected to the plunger or push rod and/or may be configured for grabbing the plunger or pull rod in order to drive the insertion component to perform the insertion movement and/or the retraction movement.

The insertion component retractor may comprise at least one latch. The term "latch" as used herein is a broad term and is to be given its ordinary and customary meaning to a person of ordinary skill in the art and is not to be limited to a special or customized meaning. The term specifically may refer, without limitation, to at least one element protruding outwards the insertion component retractor, in particular perpendicular to an insertion direction. The latch may be configured for guiding the twist of the insertion component retractor. The latch may function as a guiding wing interacting with the insertion sleeve, the guide sleeve and/or the cap. The guiding of the twist may be differentiated from a longitudinal guiding which may be performed by using a cylindrical shape of the insertion component retractor and its cylindrical counterpart within the insertion sleeve. Specifically, the latch may be configured for sliding in a groove of the insertion sleeve for guiding the twist of the insertion component retractor. The latch may be configured for interacting with other components of the insertion device such as with the ramp of the guide sleeve. The latch may protrude outwards from an outside of the insertion component retractor. For example, the insertion component retractor may form a cylindrical body. The latch may protrude from a lateral surface of the, in particular cylindrical, body of the insertion component retractor. In one embodiment, the insertion component retractor may comprise at least two latches. The two latches may be arranged opposite to each other at the outside of the insertion component retractor. The interaction of the latch with other components of the insertion device, specifically the interaction of the latch with the groove of the insertion sleeve and/or the ramp of the guide sleeve, will be outlined in further detail below.

The term "cap" as used herein is a broad term and is to be given its ordinary and customary meaning to a person of ordinary skill in the art and is not to be limited to a special or customized meaning. The term specifically may refer, without limitation, to an arbitrary shaped element configured for fully or partially enclosing one or more components of the insertion device and/or for providing protection for these one or more components, such as against mechanical influence and/or humidity. The cap may surround and/or may enclose fully or partially one or more further components, such as the insertion component retractor, the guide sleeve and/or the insertion sleeve. The term "at least partially surround," also referred to as "at least partially enclose," as used herein is a broad term and is to be given its ordinary and customary meaning to a person of ordinary skill in the art and is not to be limited to a special or customized meaning. The term specifically may refer, without limitation, to embodiments wherein the cap fully surrounds the one or more further components of the insertion device and to embodiments wherein the cap may surround at least a part of the one or more further components. For example, the cap of the insertion device may fully surround the insertion sleeve and the insertion component retractor. The cap may also at least partially surround the guide sleeve and, thus, may fully cover the guide sleeve except for a proximal end of the guide sleeve. The cap may be arranged such that it surrounds and/or encloses the further components of the insertion device, wherein a proximal side of the insertion device may be at least partially uncovered by the cap allowing contacting the user's skin with the guide sleeve and movement of the insertion component out of the insertion device. The cap when being in the proximal position may align with the proximal end of the guide sleeve. The proximal side may be the side of the insertion device providing a contact area or region with the user's skin. A distal side may be a side of the insertion device opposite of the proximal side.

The cap may be or may comprise a rigid cap, such as a rigid cap made of one or more of a plastic material, a metallic material or a cardboard material.

The cap specifically may be essentially rotationally symmetric, e.g., by having an axial rotational symmetry about an axis such as a cylinder axis or axis of extension. The term "essentially rotationally symmetric" as used herein is a broad term and is to be given its ordinary and customary meaning to a person of ordinary skill in the art and is not to be limited to a special or customized meaning. The term specifically may refer, without limitation, to the fact that the cap may be fully rotationally symmetric or may comprise at least one part being rotationally symmetric, whereas other parts of the cap may exhibit a form diverging from the rotational symmetry. The cap may be designed as a cylinder, a hemisphere or as a dome. The cap may comprise an inner structure which may not be rotationally symmetric. An outer shape of the cap may also be asymmetrical, e.g., may be shaped ergonomically to be held by a user's hand. The inner structure of the cap may be cylindrical or prismatic corresponding a structure of the insertion sleeve.

The cap may further comprise at least one latching element, specifically at the inner structure of the cap. The latching element may be configured for holding components of the insertion device together. Specifically, the latching element may interlock the cap with at least one of the other components, such as the guide sleeve, the insertion sleeve and the insertion component retractor, in particular the insertion sleeve.

The term "guide sleeve" as used herein is a broad term and is to be given its ordinary and customary meaning to a person of ordinary skill in the art and is not to be limited to a special or customized meaning. The term specifically may refer, without limitation, to an enclosure of one or more components configured for guiding at least one movement of the enclosed components. The guide sleeve may fully or partially enclose the insertion component retractor and/or an insertion sleeve. The guide sleeve may be partially enclosed by the cap.

The guide sleeve may be essentially rotationally symmetric, specifically in accordance with the symmetry of the cap of the insertion device, in particular of the inner structure of the cap of the insertion device. For example, in case the cap may have an axial rotational symmetry about an axis such as a cylinder axis or axis of extension, the guide sleeve may have a similar axial rotational symmetry.

The guide sleeve may be movable with respect to the cap of the insertion device. For example, when using the insertion device, the guide sleeve may be configured for sliding into the cap of the insertion device. The guide sleeve, in particular the proximal end of the guide sleeve, may be in contact with the user's skin when the insertion device is used.

The term "ramp" as used herein is a broad term and is to be given its ordinary and customary meaning to a person of ordinary skill in the art and is not to be limited to a special or customized meaning. The term specifically may refer, without limitation, to an element of the guide sleeve comprising at least one inclined surface. The ramp may be arranged on an inner side of the guide sleeve. Specifically, the ramp may be arranged such that it faces the components enclosed by the guide sleeve. The ramp may protrude from the guide sleeve into an interior of the guide sleeve. The ramp may be or may comprise at least one wedge-shaped ramp. For example, the ramp may comprise two inclined surfaces in contact with each other, wherein a first inclined surface may be tilted by an angle with respect to a second inclined surface. The ramp may be configured for interacting with other components of the insertion device, specifically with the at least one latch of the insertion component retractor. The ramp may be received by the components enclosed by the guide sleeve, specifically, by the groove of the insertion sleeve. In one preferred embodiment, the guide sleeve may comprise two ramps protruding from the guide sleeve into the interior of the guide sleeve. The two ramps of the guide sleeve specifically may be arranged opposite to each other in the interior of the guide sleeve.

The term "insertion sleeve" as used herein is a broad term and is to be given its ordinary and customary meaning to a person of ordinary skill in the art and is not to be limited to a special or customized meaning. The term specifically may refer, without limitation, to an element configured for at least partially enclosing the insertion component retractor. The insertion sleeve itself may be enclosed fully or partially by the guide sleeve and the cap of the insertion device.

The insertion sleeve may be prismatic. The insertion sleeve may be essentially rotationally symmetric, specifically in accordance with the symmetry of the cap and the guide sleeve. For example, the cap and the guide sleeve may have an axial rotational symmetry about an axis such as a cylinder axis or axis of extension, the insertion sleeve may have a similar axial rotational symmetry. The insertion sleeve may be configured for guiding the insertion component retractor. For example, for guiding a cylindrical-shaped insertion component retractor, the insertion sleeve may comprise a rotational symmetric hollow center. The rest of the insertion sleeve may have an irregular cross section.

The insertion sleeve may comprise at least one receptacle. The receptacle may be arranged at a distal end of the insertion sleeve. The distal end of the insertion sleeve may refer to a part of the insertion sleeve being distal to user's skin. The receptacle may have at least one opening. The insertion component and/or the insertion component retractor may extend at least partially through the opening. The term "at least partially extend" as used herein is a broad term and is to be given its ordinary and customary meaning to a person of ordinary skill in the art and is not to be limited to a special or customized meaning. The term specifically may refer, without limitation, to the fact that the insertion component retractor and/or the insertion component may fully extend through the opening of the receptacle or, alternatively, a part of the insertion component retractor and/or of the insertion component may extend through the opening of the receptacle. Specifically, the insertion component, in particular, the plunger fixedly connected to the insertion component, may at least partially extend through the opening such that at least one part of the insertion component may be arranged below the opening, wherein at least one other part may be arranged above the opening. "Below the opening" in this context means in a proximal position and "above the opening" in this context means in a distal position, wherein the proximal position and the distal position are defined relative to the user's skin when the insertion device is in use. This is defined in more detail below. For example, the plunger fixedly connected to the insertion component may extend through the opening of the insertion sleeve while other parts of the insertion component, specifically the insertion cannula or the insertion needle, may be arranged below the opening and may be surrounded by the insertion sleeve. The insertion sleeve may comprise two receptacles, such as one receptacle for the insertion component retractor, which may be open to the distal end of the insertion sleeve, and one further receptacle for the medical device, which may be open to a proximal end of the insertion sleeve. The proximal end may be opposite to the distal end of the insertion sleeve. In particular, the receptacle for the insertion component retractor may be connected to the further receptacle for the medical device by the opening.

The insertion sleeve may comprise the at least one groove. The groove which may be configured for guiding the latch of the insertion component retractor, specifically, in a rotational way for twisting the insertion component retractor. The groove may be configured for guiding the movement of the insertion component retractor by restricting a direction of movement of the latch. The term "groove" as used herein is a broad term and is to be given its ordinary and customary meaning to a person of ordinary skill in the art and is not to be limited to a special or customized meaning. The term specifically may refer, without limitation, to one or more of a slot, a trench cut and/or an opening of the insertion sleeve. The groove may be a trench cut in the insertion sleeve such that the groove may only partially cut into the insertion sleeve. Alternatively and/or additionally, the groove may be an opening of the insertion sleeve such that the groove may fully cut the insertion sleeve. The groove of the insertion sleeve may extend essentially parallel to an axis of extension of the insertion sleeve. The term "essentially parallel" as used herein is a broad term and is to be given its ordinary and customary meaning to a person of ordinary skill in the art and is not to be limited to a special or customized meaning. The term specifically may refer, without limitation, to the fact that the groove may extend parallel to the axis of extension of the insertion sleeve or, alternatively, may extend in a direction diverging from the axis of extension. Specifically, the groove may extend parallel to the axis of extension and may vary in one or more locations from the direction parallel to the axis of extension. For example, the groove may comprise at least one edge and, thus, may diverge from the axis of extension at the location of the edge. The edge may be z-shaped edge. Additionally and/or alternatively, the groove may be tilted about an angle with respect to the axis of extension of the insertion sleeve.

For inserting the medical device, the cap, the insertion component retractor and the insertion sleeve are movable relative to the guide sleeve from the distal position to the proximal position. The guide sleeve may be regarded as fix or non-moving component of the insertion device since the guide sleeve is positioned on the user's skin. The other components, such as the medical device, the insertion component, the insertion component retractor, the insertion sleeve and the cap may move in a proximal direction relative to the skin of the user relative to the guide sleeve.

The term "distal position" as used herein is a broad term and is to be given its ordinary and customary meaning to a person of ordinary skill in the art and is not to be limited to a special or customized meaning. The term specifically may refer, without limitation, to a position specification indicating a position of the insertion device and/or any parts thereof in relation to the user in which the insertion component and/or the cap are furthermost from the proximal side of the insertion device. Specifically, for inserting the medical device, the insertion device may be brought into contact with a skin site of the user. The distal position may refer to a position being distanced to the skin site of the user. The distal position may be an initial position prior to the insertion movement of the insertion device and/or any parts thereof. Each component of the insertion device may have its own and/or individual distal position. For example, the cap, the insertion component retractor and the insertion sleeve may have their own and/or individual distal positions, respectively. Prior to insertion, the cap, the insertion component retractor and the insertion sleeve may be in their distal position and may be ready for inserting the medical device into the body tissue of the user. After insertion, the cap and the insertion component retractor may be moved back to their distal positions, respectively, and the insertion component may be retracted from the body tissue when the insertion component retractor may be back in its distal position.

The term "proximal position" as used herein is a broad term and is to be given its ordinary and customary meaning to a person of ordinary skill in the art and is not to be limited to a special or customized meaning. The term specifically may refer, without limitation, to a position specification indicating a position of the insertion device and/or any parts thereof in relation to the user in which the insertion component and/or the cap are closest to the proximal side of the insertion device. Specifically, for inserting the medical device, the insertion device may be brought into contact with the skin site of the user. The proximal position may refer to a position being in close proximity to the skin site of the user. Each component of the insertion device may have its own and/or individual proximal position. For example, the cap, the insertion component retractor and the insertion sleeve may have their own and/or individual proximal positions, respectively. In case the cap, the insertion component retractor and the insertion sleeve are in their proximal position, the medical device may be inserted into the body tissue of the user. During insertion of the medical device, the guide sleeve may be in contact with the skin site of the user and, thus, may be, during insertion, in its proximal position.

The movement of the cap together with the insertion component retractor and the insertion sleeve from its distal position to its proximal position may be initiable by an action of the user. Specifically, the action of the user may be or may comprise application of a force to the cap by the user such as by manual pressing and/or pushing the cap downward to the proximal position, in particular to the user's skin. The insertion device may be a mechanical insertion device which preferably may be operated by hand, preferably without the need of electrical or electromechanical actuators. However, other embodiments are feasible.

The ramp of the guide sleeve is configured to twist the insertion component retractor relative to the guide sleeve and the insertion sleeve when the cap is moved from its distal position to its proximal position. The term "twist" as used herein is a broad term and is to be given its ordinary and customary meaning to a person of ordinary skill in the art and is not to be limited to a special or customized meaning. The term specifically may refer, without limitation, to a rotational movement of the insertion component retractor with respect to an axis of rotation. The twist may be a rotational movement of the insertion component retractor upon itself, e.g., a rotational movement about the axis of rotation being congruent with the axis of extension of the cylindrical body of the insertion component retractor. Specifically, the insertion component retractor may be essentially rotationally symmetric and the twist may be a rotational movement about a symmetry axis of the insertion component retractor. The twist may be a twist about an angle less than 90°, specifically less than 45°, more specifically less than 15°. Other embodiment are feasible, wherein the twist may be about an angle of more 90° or even more than 180°.

During insertion, movement of the insertion component retractor from its proximal position to its distal position may be prevented by the inner structure of the cap and the force applied by the user on the cap. The inner structure may be or may comprise a stopping and/or blocking element configured for receiving the latch of the insertion component retractor and for preventing movement of the insertion component retractor from its proximal position to its distal position during insertion, specifically by blocking movement of the latch. During insertion, the components of the insertion device move towards each other. Close before reaching the proximal position of the insertion component retractor, the ramp of the guide sleeve may be in contact with the latch of the insertion component retractor. In this situation, the ramp may be configured for twisting the latch thereby twisting the insertion component retractor. Specifically, the ramp of the guide sleeve may be configured for forcing the insertion component retractor to twist by guiding the latch to move within the groove of the insertion sleeve.

The insertion movement may be completed when the cap is in its proximal position. The cap when being in the proximal position may align with the proximal end of the guide sleeve.

The movement of the cap together with the insertion component retractor from its proximal position to its distal position may be initiable by relieving the action of the user. Specifically, the user may reduce or may stop applying the force to the cap thereby initiating movement of the cap together with the insertion component retractor from its proximal position to its distal position. The term "relieving" as used herein is a broad term and is to be given its ordinary and customary meaning to a person of ordinary skill in the art and is not to be limited to a special or customized meaning. The term specifically may refer, without limitation, to a process of completely stopping applying the action and to a process of partially stopping applying the action such as by reducing or diminishing the force.

The elastic member may be configured for driving the insertion component retractor to move from its proximal position to its distal position. Specifically, the elastic member may be configured for retracting the insertion component retractor after insertion of the medical device. The term "elastic member" as used herein is a broad term and is to be given its ordinary and customary meaning to a person of ordinary skill in the art and is not to be limited to a special or customized meaning. The term specifically may refer, without limitation, to an element which, when being compressed or stretched from its resting position, may exert a force opposing to the compression or stretch. The elastic member may be configured for applying the force to one or more further elements of the insertion device. Specifically, the elastic member may be compressed or stretched when the medical device is inserted into the body tissue or, alternatively, the elastic member may already be in a compressed or stretched state, such as in a pre-tensioned state, prior to use of the insertion device. The elastic member may be or may comprise at least one spring. The spring may be connected to the insertion component retractor. The spring may be pre-tensioned, specifically in between the insertion sleeve and the insertion component retractor. In particular, the elastic member, preferably the spring, is located in the distal receptacle of the insertion sleeve. Provided that the user applies the force to the cap, the spring may not be able to move the insertion component retractor and the cap from their proximal position to their distal position, respectively. The spring may be actuable by releasing a force applied to the cap. Specifically, the spring may be configured to drive the movement of the insertion component retractor and of the cap from their proximal positions to their distal positions in a situation in which the latch of the insertion component retractor has moved beyond the at least one edge of the at least one groove, i.e., in the proximal position of the insertion component retractor, when the force applied to the insertion device is reduced. In the distal position, the latch may be released from the groove of the insertion sleeve and the insertion component retractor may twist further to be received by the inner structure of the cap. The insertion component may be fully retracted from the body tissue.

As outlined above, the insertion device may comprise the at least one plunger fixedly connected to the insertion component. The plunger may be also referred to as needle head. The insertion component retractor may be connected to the plunger. The insertion component retractor may be configured for engaging with the plunger when being moved from its proximal position to its distal position. Specifically, the insertion component retractor may engage with the plunger by using the finger, gripper, hook, pincer or the like. During retraction, the insertion component retractor may be moved from its proximal position to its distal position thereby engaging to the plunger such that the plunger may be moved together with the insertion component fixedly engaged with the plunger from the proximal to the distal position. Thus, the insertion component may be retracted by the movement of the insertion component retractor from its proximal position to its distal position.

A short time delay of at least 100 ms may occur after the insertion and before the retraction of the insertion component starts. In particular, when the insertion device is applied to the skin site of the user, the skin typically bulges towards the interior of the insertion device. The short time delay between the insertion device, in particular the insertion component, being in the proximal position and the insertion device, in particular the insertion component, being moved back in its distal position allows application of pressure onto the bulged skin. Thereby, sliding of the insertion component together with the medical device into the skin is facilitated and enables the skin of the user to slide over the entire length of the insertion component and the medical device.

The insertion device according to this disclosure allows the skin to be more tensioned compared to insertion devices known from the prior art. This has the effect that the insertion of the medical device into the body tissue of the user may be more reliable. Thus, the insertion device according to this disclosure may ensure a safe and user-friendly insertion of the medical device.

The insertion device may further comprise at least one safety lock. The term "safety lock" as used herein is a broad term and is to be given its ordinary and customary meaning to a person of ordinary skill in the art and is not to be limited to a special or customized meaning. The term specifically may refer, without limitation, to a device or combination of devices configured for performing at least one safety function. The safety lock may be configured for preventing reuse of the insertion device, in particular after insertion of the medical device and retraction of the insertion component. The safety lock may be configured for preventing an unwanted re-actuation of the insertion device. The safety lock may be configured for locking the insertion device, wherein in the locked insertion device an unwanted reuse may be prevented.

The safety lock may comprise one or more components being mounted at different components of the insertion device. For example, at least one safety notch may be arranged at the insertion sleeve and being configured for receiving the latch of the insertion component retractor. The safety notch may be arranged adjacent to the groove of the insertion sleeve such that the latch may be received in the safety notch when the groove guides the latch and the insertion component retractor from its proximal position to its distal position. The latch may be received by the safety notch such that re-movement thereof may be prevented. Specifically, the safety notch may block re-movement of the latch and the insertion component retractor when the user applies a force to the cap of the insertion device once more. By preventing re-movement of the insertion component retractor, at the same time re-movement of the insertion component is prevented. Thus, the risk of unintentional injuries may be minimized.

The insertion device may further be configured for receiving a sensor patch and for attaching the sensor patch to the skin site of the user. The insertion device may be configured for attaching and/or arranging the sensor patch to the skin site of the user, in particular simultaneously with the insertion of the insertion component into the body tissue of the user. In particular, the sensor patch may be comprised in a receptacle of the insertion sleeve, in particular in a proximally positioned receptacle of the insertion sleeve. Thus, the sensor patch may be configured to move together with the insertion sleeve and to be released from the insertion sleeve when the insertion sleeve is in its proximal position. The term "sensor patch" as used herein is a broad term and is to be given its ordinary and customary meaning to a person of ordinary skill in the art and is not to be limited to a special or customized meaning. The term specifically may refer, without limitation, to an element configured for being attached to the skin site of the user. In particular, the sensor patch may have a flat base which is configured for being attached to the skin site of the user. The sensor patch may comprise the electronics unit which may be configured for being connected to the medical device, specifically to the analyte sensor. The electronics unit may have large dimensions compared to the analyte sensor and to the insertion component. The diameter of the insertion component may be as large as 1 mm while the sensor patch may extend for up to 2 to 4 cm. The sensor patch may comprise at least one adhesive means for being attached to the skin site of the user such as plaster or the like. The sensor patch may remain attached to the skin site of the user after the medical device was inserted into the body tissue of the user. The insertion component may protrude through the sensor patch received by the insertion device. The insertion component retractor may be configured for grabbing the insertion component in the sensor patch prior to insertion of the medical device.

In particular if the insertion device comprises a sensor patch, the insertion of the medical device is facilitated and more reliable. When the insertion device is applied to the skin, the skin typically bulges toward the interior of the insertion device. The short time delay between the insertion device, in particular the insertion component, being in the proximal position and the insertion device, in particular the insertion component, being moved back in its distal position allows application of pressure onto the bulged skin by the sensor patch. This compensates the inward bulging of the skin as well as the indenting of the inward bulged skin by the insertion component. Thus, the sliding of the insertion component together with the medical device into the skin is facilitated.

In a further aspect of this disclosure, a method for inserting a medical device into a body tissue of a user is disclosed by using at least one insertion device according to any one of the embodiments disclosed above and/or according to any one of the embodiments disclosed in further detail below. Thus, for possible definitions and options, reference may be made to the disclosure of the insertion device according to this disclosure. The method comprises the following steps which specifically may be performed in the given order. The method may comprise further method steps which are not listed.

The method comprises:
a) inserting the medical device into the body tissue of the user by applying a force on the cap of the insertion device thereby moving the insertion component, the cap, the insertion component retractor and the insertion sleeve relative to the guide sleeve from a distal position to a proximal position; and
b) retracting the insertion component by relieving the force applied to the cap thereby moving the cap from its proximal position to its distal position, thereby moving the insertion component retractor from its proximal position to its distal position.

The movement of the cap together with the insertion component retractor and the insertion sleeve from its distal position to its proximal position may be initiated by action of the user, specifically by applying a force to the cap of the insertion device. The force may be applied by the user of the insertion device before and during the insertion of the medical device. The insertion of the medical device may be started by setting the guide sleeve, in particular the proximal end of the guide sleeve, in contact with the skin of the user, specifically at an insertion site. Thus, step a) of the method may comprise applying the insertion device to the skin site of the user, in particular applying the guide sleeve of the insertion device to the skin site of the user.

Prior to insertion, the insertion sleeve may be in its distal position and may be at least partially enclosed by the guide sleeve in its distal position. The cap may be in contact to the insertion sleeve, specifically at the distal end of the insertion sleeve. Prior to insertion, the insertion component retractor may be in its starting position and may be at least partially enclosed by the insertion sleeve. The starting position of the insertion component retractor is at a proximal position relative to the insertion sleeve. The elastic member may be in between the insertion component retractor and the insertion sleeve and may be at full tension. The insertion component retractor may be locked in this position by the at least one latch which may be received by the edge in the groove of the insertion sleeve.

When the user exerts the force to the cap, the arm of the user, which applies the force to the cap, may accelerate in proximal direction, specifically towards the skin of the user. In an embodiment, to accelerate in proximal position, it may be necessary to overcome an initial force. After the initial force is overcome, the force which is required to move the insertion component, the cap, the insertion component retractor and the insertion sleeve relative to the guide sleeve may be lower than the initial force. Shortly before the insertion sleeve reaches its proximal position, the latch of the insertion component retractor may get in contact with the at least one ramp of the guide sleeve, wherein the ramp may specifically protrude inwardly the guide sleeve. The insertion component retractor may be twisted by the interaction of the ramp and the latch. The latch may fall loose from the edge in the groove of the insertion sleeve and may get in contact to the inner structure of the cap. The arm of the user may get stopped by the contact between the insertion sleeve, in particular the sensor patch which is in an embodiment comprised in the insertion device, and the skin of the user. Because of the kinetic energy of the mass of the arm, this stopping may cause pressure of the insertion sleeve, in particular of the sensor patch which is in an embodiment comprised in the insertion device, against the skin of the user.

Step b) may comprise relieving the force applied to the cap. Triggered by relieving the force applied to the cap, the insertion component may be moved back from the skin site of the user. When the user releases the force the elastic element, in particular the spring may force the insertion component retractor and in consequence the cap into movement to the distal position. The latch may slide along the groove in the insertion sleeve until the insertion component may be totally retracted from the body tissue of the user. The latch may be forced by the inner structure of the cap and the spring may force to twist the insertion component retractor even further into a position where the latch may not be able to move any further, specifically into a position where the insertion component retractor cannot move in proximal direction any more. The insertion component retractor cannot move in proximal direction any more since the latch may be received by the safety lock, more specifically by the safety notch of the insertion sleeve. Thus, after insertion of the medical device, the insertion component may be safely locked by the safety lock of the insertion device.

The insertion device according to this disclosure may change the order of movements compared to know insertion devices. In known insertion devices the insertion component may exert a force to the skin in which the medical device shall be inserted. The skin bulges inwardly under this force. In known insertion devices near the end of the insertion movement the insertion component is retracted. Because of the inward bulging of the skin and the indenting of the skin under the attack of the insertion component, the medical device, however, may not fully be inserted when the insertion component starts to disappear rapidly. Thus, the result may be a not or just partly inserted medical device. The insertion device according to this disclosure compensates this indenting of the skin by applying pressure, in particular with the sensor patch to the skin while the insertion element still protrudes in its full length from the insertion device into the skin. This may ensure a reliable insertion of the medical device into the body tissue of the user. After this, the insertion component may be retracted.

In an embodiment, the method for inserting a medical device into a body tissue of the user by using an inventive insertion device comprising a sensor patch, comprises the following steps:
a1) bringing the insertion device, in particular the proximal end of the guide sleeve in contact with a skin site of a user,
a) inserting the medical device into the body tissue of the user by applying a force on the cap of the insertion device thereby moving the insertion component, the cap, the insertion component retractor and the insertion sleeve relative to the guide sleeve from a distal position to a proximal position,
b1) applying pressure to the skin site of the user with the sensor patch,
b) retracting the insertion component by relieving the force applied to the cap, thereby moving the cap from its proximal position to its distal position, thereby moving the insertion component retractor from its proximal position to its distal position.

The methods and devices according to this disclosure provide a large number of advantages over known methods and devices. Specifically, the insertion device according to this disclosure may enable a user activated retraction of the insertion component from the body tissue of the user and, thus, may allow enhancing reliability of the insertion of the medical device into the body tissue of the user.

Summarizing and without excluding further possible embodiments, the following embodiments may be envisaged:

Embodiment 1: An insertion device for inserting a medical device into a body tissue of a user, the insertion device comprising:
  i) the medical device;
  ii) an insertion component configured for inserting the medical device into the body tissue;
  iii) an insertion component retractor;
  iv) a cap;
  v) a guide sleeve comprising at least one ramp;
  vi) an insertion sleeve; and
  vii) an elastic member;
wherein, for inserting the medical device, the cap, the insertion component retractor and the insertion sleeve are movable relative to the guide sleeve from a distal position to a proximal position, wherein the ramp of the guide sleeve is configured to twist the insertion component retractor relative to the guide sleeve and the insertion sleeve when the cap is moved from its distal position to its proximal position, wherein the cap is movable from its proximal position to its distal position, thereby the insertion component retractor is moved from its proximal position to its distal position.

Embodiment 2: The insertion device according to embodiment 1, wherein the movement of the cap together with the insertion component retractor and the insertion sleeve from its distal position to its proximal position is initiable by an action of the user.

Embodiment 3: The insertion device according to any one of embodiments 1 or 2, wherein the movement of the cap together with the insertion component retractor from its proximal position to its distal position is initiable by relieving the action of the user.

Embodiment 4: The insertion device according to any one of embodiments 1 to 3, wherein before reaching the proximal position of the insertion component retractor, the ramp of the guide sleeve is in contact with a latch of the insertion component retractor and the ramp is configured for twisting the latch thereby twisting the insertion component retractor.

Embodiment 5: The insertion device according to embodiment 4, wherein the insertion sleeve comprises at least one groove, wherein the groove is configured for guiding the latch of the insertion component retractor, wherein the groove comprises at least one edge.

Embodiment 6: The insertion device according to embodiment 5, wherein the ramp of the guide sleeve is configured for forcing the insertion component retractor to twist by guiding the at least one latch to move within the groove of the insertion sleeve.

Embodiment 7: The insertion device according to any one of embodiments 1 to 6, wherein the elastic member is configured for driving the insertion component retractor to move from its proximal position to its distal position, wherein the elastic member comprises at least one spring, wherein the spring is connected to the insertion component retractor, wherein the spring is pre-tensioned and is actuatable by releasing a force applied to the cap.

Embodiment 8: The insertion device according to embodiment 7, wherein the at least one spring is configured to drive the movement of the insertion component retractor from its proximal position to its distal position and thereby drive the movement of the cap from its proximal position to its distal position.

Embodiment 9: The insertion device according to any one of embodiments 1 to 8, wherein the cap when being in the proximal position aligns with a proximal end of the guide sleeve.

Embodiment 10: The insertion device according to any one of embodiments 1 to 9, wherein the insertion device further comprises at least one safety lock, wherein the safety lock is configured for preventing re-movement of the insertion component retractor after being moved to its distal position.

Embodiment 11: The insertion device according to any one of embodiments 1 to 10, wherein the medical device comprises at least one analyte sensor for detecting at least one analyte in a bodily fluid of a user.

Embodiment 12: The insertion device according to embodiment 11, wherein the at least one analyte sensor comprises at least one two-electrode sensor.

Embodiment 13: The insertion device according to any one of embodiments 1 to 12, wherein the insertion device comprises a sensor patch.

Embodiment 14: The insertion device according to embodiment 13, wherein the sensor patch comprises a flat base which is configured for being attached to a skin site of the user.

Embodiment 15: The insertion device according to embodiment 13 or 14, wherein the insertion device is configured for applying pressure to a skin site of the user by the sensor patch.

Embodiment 16: A method for inserting a medical device into a body tissue of a user by using at least one insertion device according to any one of embodiments 1 to 15, wherein the method comprises:
  a) inserting the medical device into the body tissue of the user by applying a force on the cap of the insertion device thereby moving the insertion component, the cap, the insertion component retractor and the insertion sleeve relative to the guide sleeve from a distal position to a proximal position; and
  b) retracting the insertion component by relieving the force applied to the cap thereby moving the cap from its proximal position to its distal position, thereby moving the insertion component retractor from its proximal position to its distal position.

Embodiment 17: A method for inserting a medical device into a body tissue of the user by using at least one insertion device according to any one of embodiments 1 to 12, wherein the insertion device comprises a sensor patch, wherein the method comprises the following steps:
  a1) bringing the insertion device, in particular the proximal end of the guide sleeve in contact with a skin site of a user,
  a) inserting the medical device into the body tissue of the user by applying a force on the cap of the insertion device thereby moving the insertion component, the cap, the insertion component retractor and the insertion sleeve relative to the guide sleeve from a distal position to a proximal position,
  b1) applying pressure to the skin site of the user with the sensor patch, b) retracting the insertion component by relieving the force applied to the cap, thereby moving the cap from its proximal position to its distal position, thereby moving the insertion component retractor from its proximal position to its distal position.

Embodiment 18: The method according to embodiment 16 or 17, wherein the movement of the cap together with the insertion component retractor and the insertion sleeve from its distal position to its proximal position is initiated by action of the user.

Embodiment 19: The method according to any one of embodiments 16 to 18, wherein the movement of the cap together with the insertion component retractor from its proximal position to its distal position is initiated by relieving action of the user.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
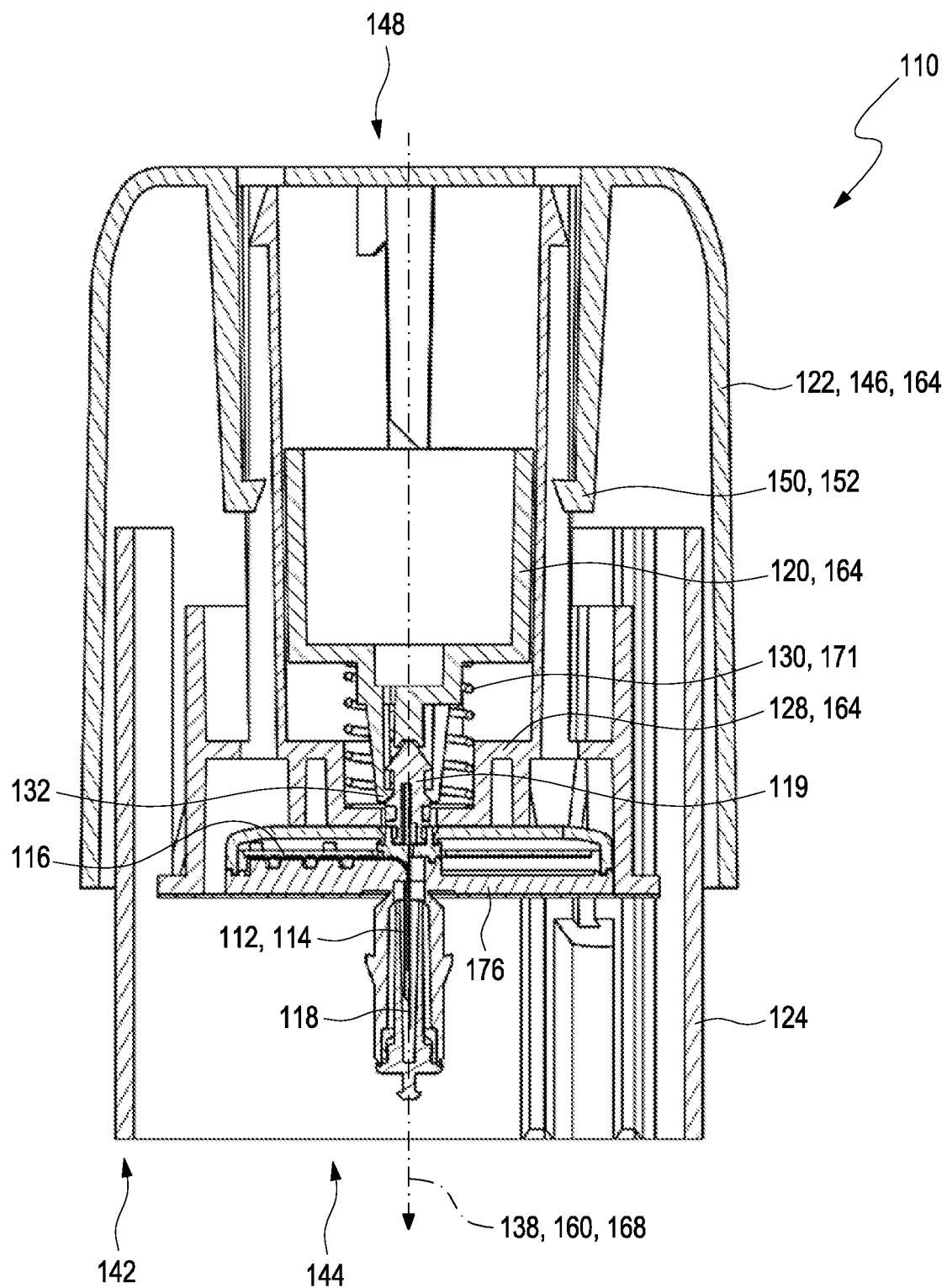
FIGS. 1A to 1C show two longitudinal-sectional views and a cross-sectional view of an embodiment of an insertion device according to this disclosure.
Figure 1:
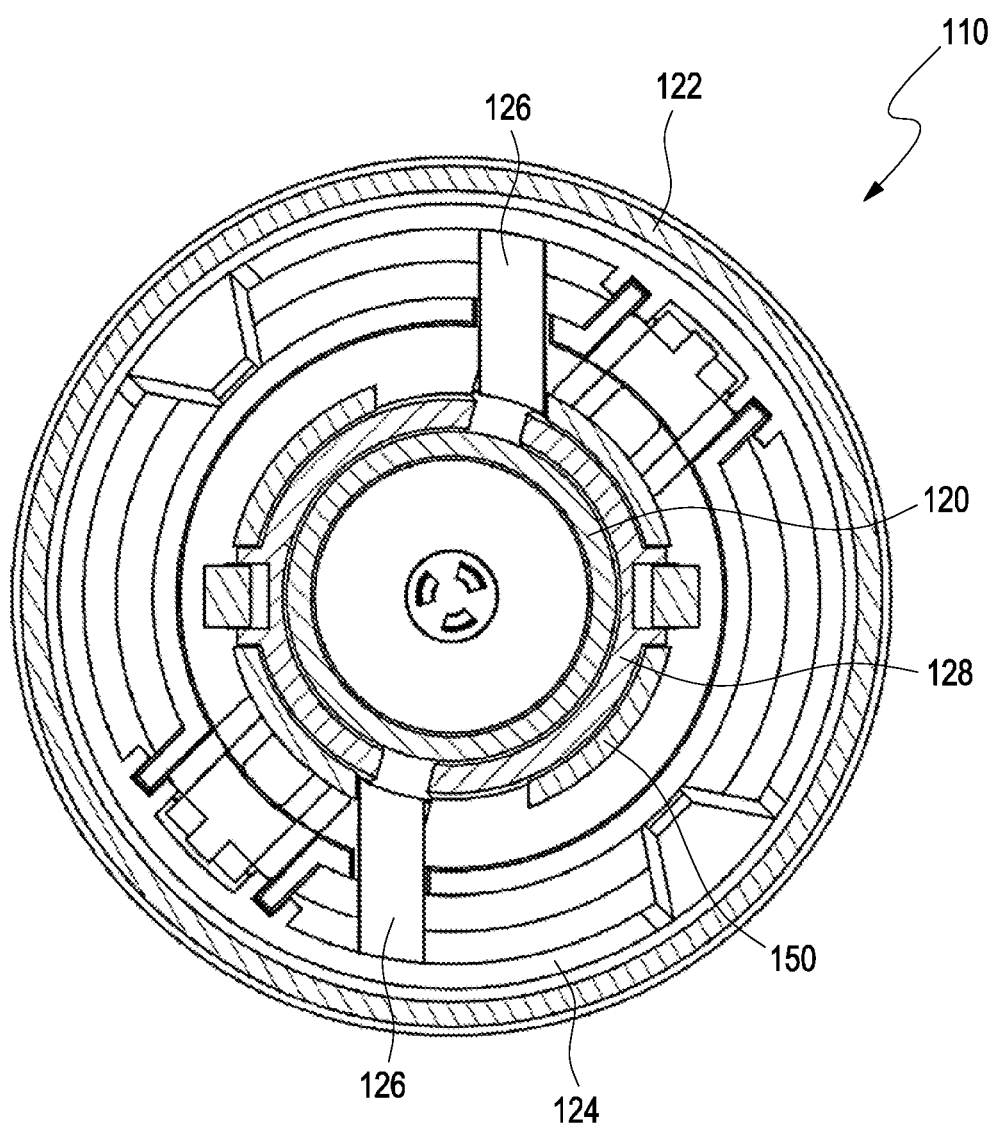
Figure 1C:
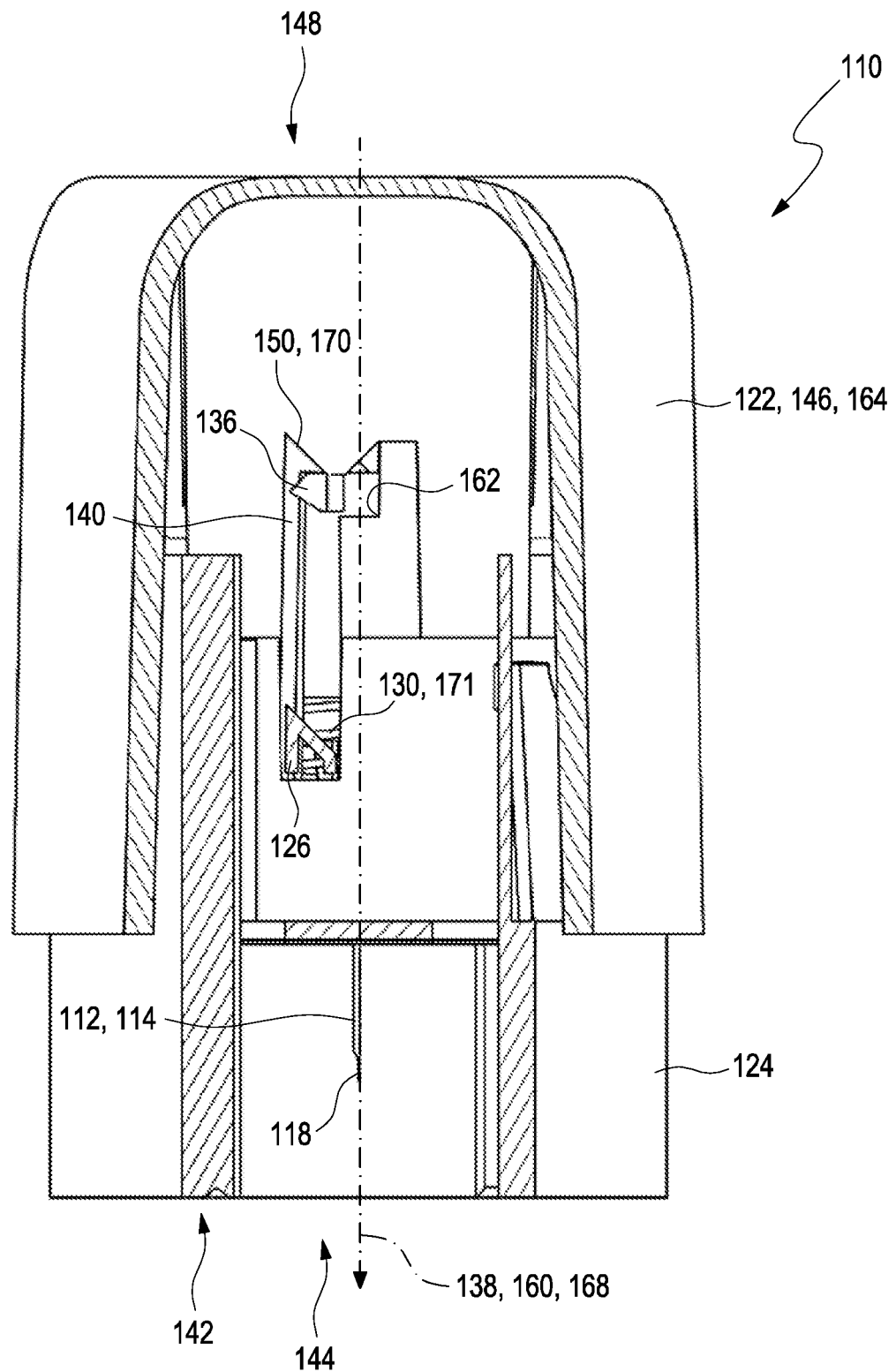

FIGS. 1A to 1C show an exemplary embodiment of an insertion device 110 according to this disclosure for inserting a medical device 112 into a body tissue of a user. In FIG. 1A, the insertion device 110 is shown in a longitudinal-sectional view, wherein the longitudinal-sectional view passes through a median plane of the insertion device 110. In FIG. 1B a cross-sectional view is shown. In FIG. 1C, a longitudinal-sectional view in front of the median plane of the insertion device 110 is shown. FIGS. 1A to 1C show the insertion device 110 prior to insertion of the medical device 112.

The medical device 112 may be an arbitrary element or article being configured for use in the field of medical technology, specifically in the field of medical analytics or medical diagnostics. The medical device 112 may be configured for performing at least one medical function and/or for being used in at least one medical process, such as one or more of a therapeutic process, a diagnostic process or another medical process.

For example, the medical device 112 may be or may comprise at least one analyte sensor 114 for detecting at least one analyte in a bodily fluid of a user, such as in a bodily fluid contained in a body tissue of the user. The analyte sensor 114 may be configured for being used in qualitatively and/or quantitatively detecting the at least one analyte. The analyte may be a chemical and/or biological substance which takes part in the metabolism of the body of the user. Specifically, the analyte may be a metabolite or a combination of two or more metabolites. As an example, the analyte may be selected from the group consisting of: glucose, lactate, triglycerides, and cholesterol. Still, other analytes or combinations of two or more analytes may be detected. The body tissue specifically may be or may comprise fatty tissue and/or interstitium. Other types of body tissue, however, are feasible.

The analyte sensor 114 may be a sensor which is capable of qualitatively or quantitatively detecting the presence and/or the concentration of the at least one analyte. For example, the analyte sensor 114 may be an electrochemical analyte sensor. The analyte sensor 114 may comprise at least two electrodes. Specifically, the analyte sensor 114 may comprise at least one two-electrode sensor. The two-electrode sensor may comprise precisely two electrodes, such as a working electrode and at least one further electrode such as a counter electrode, in particular a working electrode and a combined counter/reference electrode. The working electrode may comprise a working electrode pad and, optionally, at least one test chemical disposed thereon. The counter electrode may comprise a conductive electrode pad. Additionally and optionally, one or more redox materials may be disposed thereon. The analyte sensor 114 may further comprise one or more leads for electrically contacting the electrodes. The leads may, during insertion or at a later point in time, be connected to an electronics unit 116, such as one or more measurement devices adapted for measuring electrical currents and/or electrical voltages, such as to one or more potentiostats. Preferably, the leads already connected to the electronics unit 116 before insertion of the analyte sensor 114.

Specifically, the analyte sensor 114 may be a strip-shaped analyte sensor having a flexible substrate and the electrodes disposed thereon. As an example, the analyte sensor 114 may have a total length of 5 mm to 50 mm, specifically a total length of 7 mm to 30 mm.

The analyte sensor 114 may further comprise a biocompatible cover, such as a biocompatible membrane which fully or partially covers the analyte sensor 114 and which prevents the test chemical from migrating into the body tissue and which allows for a diffusion of the bodily fluid and/or the analyte to the electrodes.

Other embodiments of electrochemical analyte sensors 114, such as three-electrode sensors, may be feasible. For example, the three-electrode sensor may comprise, in addition to the working electrode and the counter electrode, a reference electrode.

In another embodiment, the analyte sensor 114 may be an optical analyte sensor. For example, the analyte sensor 114 may comprise a flexible light guide with glucose sensitive coating at its end and/or a tube like carrier with functional elements at inner or outer walls. Other embodiments of the analyte sensor 114 may be possible too. For potential embodiments of analyte sensors 114, reference may be made to the above-mentioned prior art documents.

In another embodiment not depicted here, for example, the medical device 112 may be or may comprise at least one infusion cannula. The infusion cannula may be or may comprise a hollow tube configured for delivering and/or infusing a medication, in particular insulin, into the body tissue of the user, in particular for delivering and/or infusing insulin into the body tissue of the user.

The user may be a person using the insertion device 110. The user may be a person intending to monitor an analyte value, such as a glucose value in the person's body tissue and/or to deliver medication, such as insulin into the person's body tissue. For example, the user may be a patient suffering from a disease, such as diabetes.

The inserting of the medical device 112 may comprise one or more of transcutaneously or subcutaneously implanting and/or positioning the medical device 112 into the body tissue of the user. The medical device 112, such as the analyte sensor 114, may fully or partially be inserted into the body tissue. The insertion of the medical device 112 may be performed by using the insertion device 110. The insertion device 110 may be configured for inserting the medical device 112 into the body tissue. The insertion device 110 may be configured for transcutaneously or subcutaneously inserting the medical device 112 into the body tissue, such as by performing an incision or a puncture in a skin of the user and by transferring the medical device 112 fully or partially into the body tissue. After insertion, the medical device 112 or at least a part of the medical device 112 may remain in the body tissue of the user for a predetermined period of time, such as for several hours, specifically for one or more days, more specifically for up to one week, even more specifically for up to two weeks or even more. The medical device 112 may be configured for continuously monitoring and/or detecting the analyte in the body fluid of the user.

The insertion device 110 comprises an insertion component 118, an insertion component retractor 120, a cap 122, a guide sleeve 124 comprising at least one ramp 126, an insertion sleeve 128 and an elastic member 130.

The insertion component 118 is configured for inserting the medical device 112 into the body tissue. The insertion component 118 may be insertable at least partially into the body tissue, particularly in order to deliver or to transfer a further element. The insertion component 118 may be configured for supporting the insertion of the medical device 112. The insertion component 118 may comprise a tip or a sharp end for inserting the medical device 112 into the body tissue. The insertion component 118 may be or may comprise an insertion cannula or an insertion needle.

As outlined above, after insertion, the medical device 112 may remain in the body tissue of the user. The insertion component 118, however, may be retracted from the body tissue of the user into the insertion device 110 after inserting the medical device 112. For retracting the insertion component 118 the insertion device 110 may comprise the insertion component retractor 120. The insertion component retractor 120 may be configured for suspending the insertion component 118 during insertion movement and pull it out from the skin of the user during retraction movement. An engagement between the insertion component retractor 120 and the insertion component 118 may be loose. The engagement between the insertion component retractor 120 and the insertion component 118 may be established during a production process.

Figure 2:
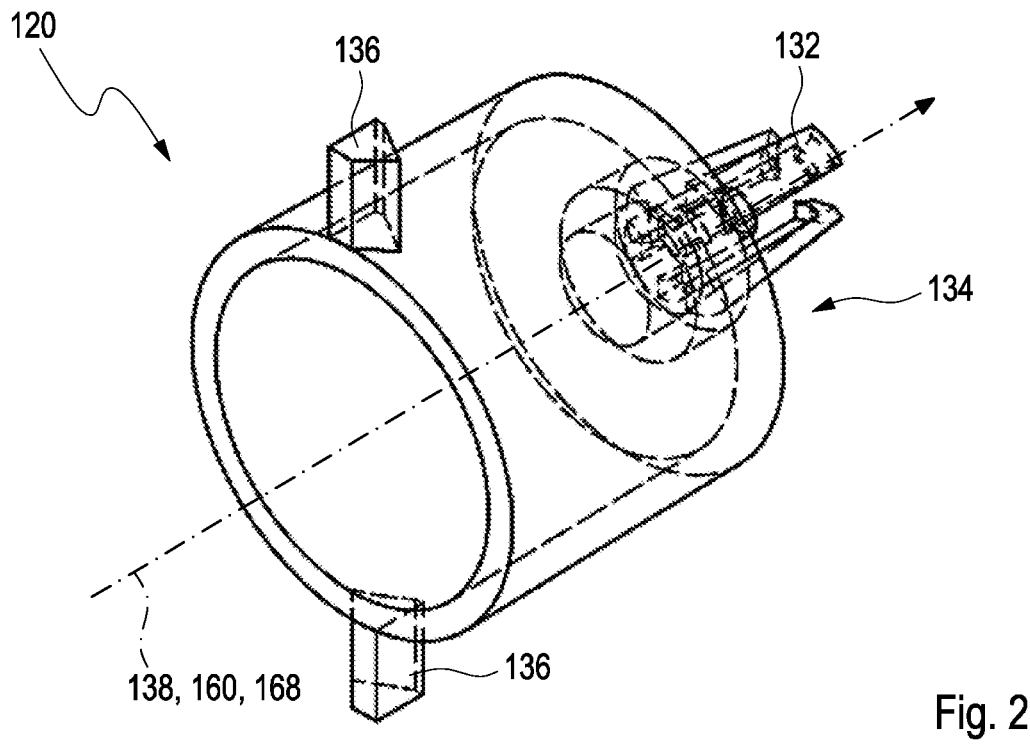
FIG. 2 shows an exemplary embodiment of an insertion component retractor in a perspective view.

FIG. 2 shows an exemplary embodiment of the insertion component retractor 120 in a perspective view.

The insertion component retractor 120 may comprise at least one finger, gripper, hook, pincer or the like configured for retracting the insertion component 118. For example, the insertion component retractor 120 may comprise two or more fingers, grippers, hooks or pincers arranged symmetrically around the insertion component 118. The finger, gripper, hook, pincer or the like may be arranged at a proximal end of the insertion component retractor 120, wherein, when the insertion device 110 is in use, the proximal end of the insertion component retractor 120 may point towards the body tissue of the user. For example, in the exemplary embodiment shown in FIG. 2, the insertion component retractor 120 may comprise three grippers 132. The grippers 132 may be arranged at a proximal end 134 of the insertion component retractor 120. The grippers 132 may be arranged symmetrically around the insertion component 118. For example, the insertion device 110 may comprise at least one plunger 119 connected to the insertion component 118. The insertion component retractor 120 may be connected to the plunger 119 and/or may be configured for grabbing the plunger 119 to drive the insertion component 118 to perform the insertion movement and/or the retraction movement. Specifically, the grippers 132 may be configured for retracting the insertion component 118, specifically by being connected and/or by grabbing the plunger 119 as will be outlined in further detail below.

The insertion component retractor 120 may further comprise at least one latch 136. The latch 136 may be at least one element protruding outwards from the insertion component retractor 120, in particular perpendicular to an insertion direction 138. The insertion component retractor 120 may form a cylindrical body. The cylindrical body may be disposed concentrically with respect to an axis of extension 160. The latch 136 may protrude outwards from a lateral surface of the cylindrical body. Specifically, the latch 136 may protrude perpendicular to the insertion direction 138, which may be essentially parallel with the axis of extension 160.

The latch 136 may be configured for guiding the twist of the insertion component retractor 120. The latch 136 may function as a guiding wing interacting with the insertion sleeve 128, the guide sleeve 124 and/or the cap 122. The guiding of the twist may be differentiated from a longitudinal guiding which may be performed by using a cylindrical shape of the insertion component retractor 120 and its cylindrical counterpart within the insertion sleeve 128. Specifically, the latch 138 may be configured for sliding in a groove 140 of the insertion sleeve 128 for guiding the twist of the insertion component retractor 120. The latch 138 may be configured for interacting with other components of the insertion device 110 such as with the ramp 126 of the guide sleeve 124. In the embodiment of FIG. 2, the insertion component retractor 120 may comprise at least two latches 136. The two latches 136 may be arranged opposite to each other at an outside of the insertion component retractor 120. The interaction of the latch 136 with other components of the insertion device 110, specifically the interaction of the latch 136 with the groove 140 of the insertion sleeve 128 and/or the ramp 126 of the guide sleeve 124, will be outlined in further detail below.

Figure 3:
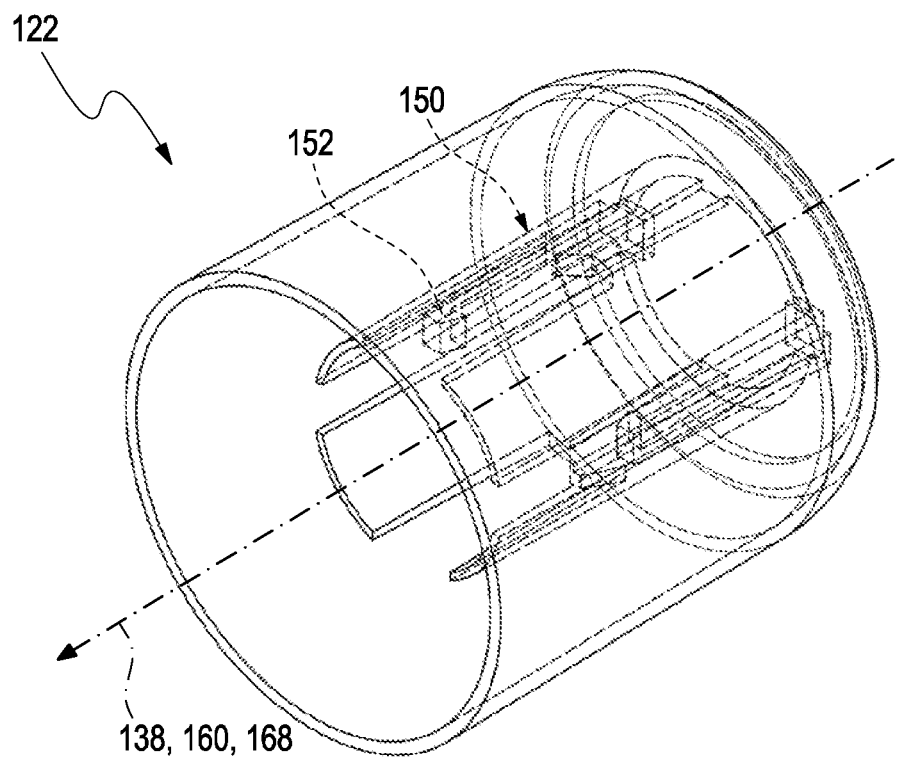
FIG. 3 shows an exemplary embodiment of a cap in a perspective view.

As shown in FIGS. 1A to 1C, the cap 122 may be an arbitrary shaped element configured for fully or partially enclosing one or more components of the insertion device 110 and/or for providing protection for these one or more components, such as against mechanical influence and/or humidity. FIG. 3 shows an exemplary embodiment of the cap 122 in a perspective view. The cap 122 may surround and/or may enclose fully or partially one or more further components, such as the insertion component retractor 120, the guide sleeve 124 and/or the insertion sleeve 128. For example, the cap 122 may fully surround the insertion sleeve 128 and the insertion component retractor 120. The cap 122 may also at least partially surround the guide sleeve 124 and, thus, may fully cover the guide sleeve 124 except for a proximal end 142 of the guide sleeve 124. The cap 122 may be arranged such that it surrounds and/or encloses the further components of the insertion device 110, wherein a proximal side 144 of the insertion device 110 may be at least partially uncovered by the cap 122 allowing contacting the user's skin with the guide sleeve 124 and movement of the insertion component 118 outside of the insertion device 110. The cap 122 when being in its proximal position 146 may align with the proximal end 142 of the guide sleeve 124. The proximal side 144 may be the side of the insertion device 110 providing a contact area or region with the user's skin. A distal side 148 may be a side of the insertion device 110 opposite of the proximal side 144.

The cap 122 may be or may comprise a rigid cap, such as a rigid cap made of one or more of a plastic material, a metallic material or a cardboard material.

The cap 122 specifically may be essentially rotationally symmetric, e.g., by having an axial rotational symmetry about an axis such as a cylinder axis or the axis of extension 160. The cap 122 may be designed as a cylinder, a hemisphere or as a dome. The cap 122 may comprise an inner structure 150 which may not be rotationally symmetric. An outer shape of the cap 122 may also be asymmetrical, e.g., may be shaped ergonomically to be held by a user's hand. The inner structure 150 of the cap 122 may be cylindrical or prismatic corresponding a structure of the insertion sleeve 128.

The cap 122 may further comprise at least one latching element 152, specifically at the inner structure 150 of the cap 122. The latching element 152 may be configured for holding components of the insertion device 110 together. Specifically, the latching element 152 may interlock the cap 122 with at least one of the other components, such as the guide sleeve 124, the insertion sleeve 128 and the insertion component retractor 120, in particular the insertion sleeve 128.

As shown in FIGS. 1A to 1C, the guide sleeve 124 may be an enclosure of one or more components configured for guiding at least one movement of the enclosed components. The guide sleeve 124 may fully or partially enclose the insertion component retractor 120 and/or an insertion sleeve 128. The guide sleeve 124 may be partially enclosed by the cap 122.

Figure 4:
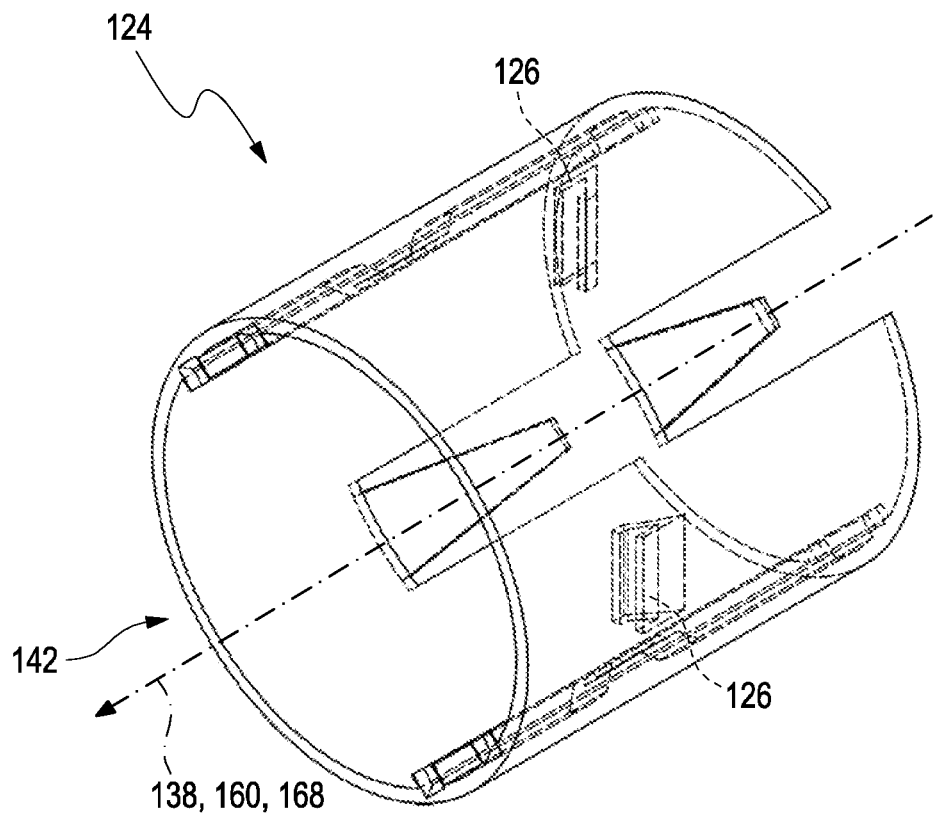
FIG. 4 shows an exemplary embodiment of a guide sleeve in a perspective view.

FIG. 4 shows an exemplary embodiment of the guide sleeve 124 in a perspective view. The guide sleeve 124 may be essentially rotationally symmetric, specifically in accordance with the symmetry of the cap 122, in particular of the inner structure of the cap 122. For example, in case the cap 122 may have an axial rotational symmetry about an axis such as a cylinder axis or the axis of extension 160, the guide sleeve 124 may have a similar axial rotational symmetry.

The guide sleeve 124 may be movable with respect to the cap 122. For example, when using the insertion device 110, the guide sleeve 124 may be configured for sliding into the cap 122. The guide sleeve 124, in particular the proximal end 142 of the guide sleeve 124, may be in contact with the user's skin when the insertion device 110 is used.

The ramp 126 of the guide sleeve 124 may comprise at least one inclined surface. The ramp 126 may be arranged on an inner side of the guide sleeve 124. Specifically, the ramp 126 may be arranged such that it faces the components enclosed by the guide sleeve 124. The ramp 126 may protrude from the guide sleeve 124 into an interior of the guide sleeve 124. The ramp 126 may be or may comprise at least one wedge-shaped ramp. For example, the ramp 126 may comprise two inclined surfaces in contact with each other, wherein a first inclined surface may be tilted by an angle with respect to a second inclined surface. The ramp 126 may be configured for interacting with other components of the insertion device 110, specifically with the at least one latch 136 of the insertion component retractor 120. The ramp 126 may be received by the components enclosed by the guide sleeve 124, specifically, by the groove 140 of the insertion sleeve 128. In FIG. 4, the guide sleeve 124 may comprise two ramps 126. The number of ramps 126 may correspond to the number of latches 136. The ramps 126 may be arranged opposite to each other in the interior of the guide sleeve 124.

As shown in FIGS. 1A to 1C, the insertion sleeve 128 may be configured for at least partially enclosing the insertion component retractor 120. The insertion sleeve 128 itself may be enclosed fully or partially by the guide sleeve 124 and the cap 122 of the insertion device 110.

Figure 5:
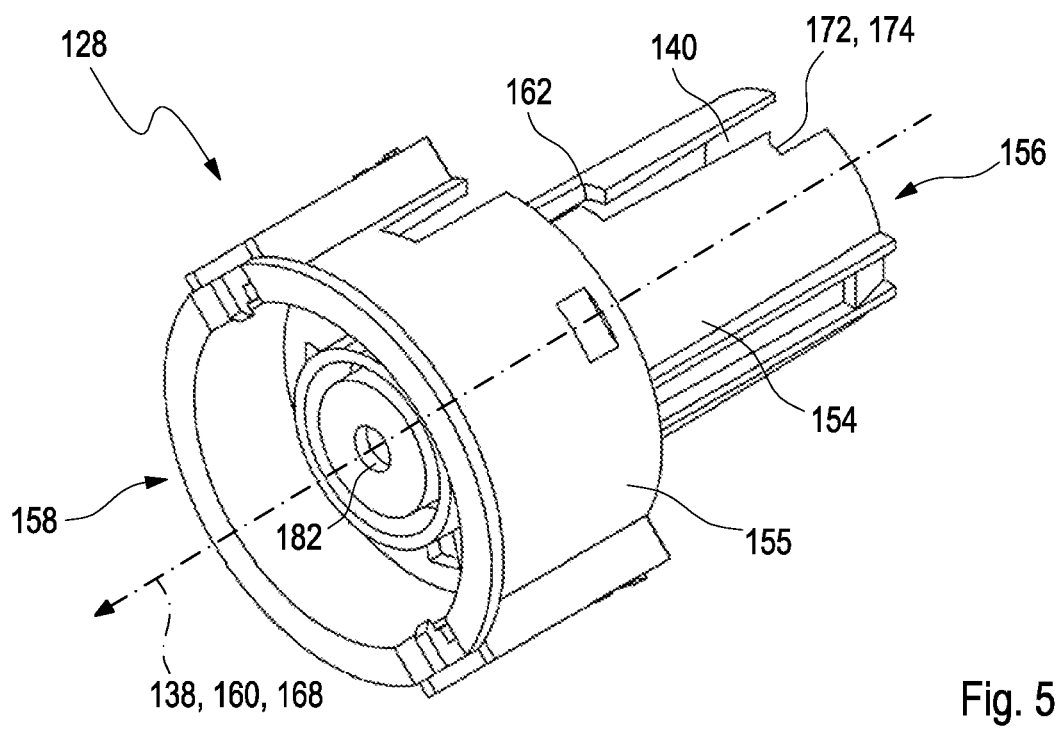
FIG. 5 shows an exemplary embodiment of an insertion sleeve in a perspective view.

FIG. 5 shows an exemplary embodiment of the insertion sleeve 128 in a perspective view. The insertion sleeve 128 may be prismatic. The insertion sleeve 128 may be essentially rotationally symmetric, specifically in accordance with the symmetry of the cap 122 and the guide sleeve 124. For example, the cap 122 and the guide sleeve 124 may have an axial rotational symmetry about an axis such as a cylinder axis or the axis of extension 160, the insertion sleeve 128 may have a similar axial rotational symmetry. The insertion sleeve 128 may be configured for guiding the insertion component retractor 120. For example, for guiding a cylindrical-shaped insertion component retractor 120, the insertion sleeve 128 may comprise a rotational symmetric hollow center. The rest of the insertion sleeve 128 may have an irregular cross section.

The insertion sleeve 128 may comprise at least one receptacle 154. The receptacle 154 may be arranged at a distal end 156 of the insertion sleeve 128. The distal end 156 of the insertion sleeve 128 may refer to a part of the insertion sleeve 128 being distal to user's skin. The receptacle 154 may have at least one opening 182. The insertion component 118 and/or the insertion component retractor 120 may extend at least partially through the opening 182. Specifically, the insertion component 118 may at least partially extend through the opening 182 such that at least one part of the insertion component 118 may be arranged below the opening 182, wherein at least one other part may be arranged above the opening 182. For example, the plunger 119 fixedly connected to the insertion component 118 may extend through the opening 182 of the insertion sleeve 128 while another part of the insertion component 118, specifically the insertion cannula or the insertion needle, may be arranged below the opening 182 and may be surrounded by the insertion sleeve 128. As shown in FIG. 5, the insertion sleeve 128 may comprise two receptacles 154, such as one receptacle 154 for the insertion component retractor 120, which may be open to the distal end 156 of the insertion sleeve 128, and one further receptacle 155 for the medical device 112, which may be open to a proximal end 158 of the insertion sleeve 128. The proximal end 158 may be opposite to the distal end 156 of the insertion sleeve 128.

The insertion sleeve 128 may comprises the at least one groove 140. The groove 140 which may be configured for guiding the latch 136 of the insertion component retractor 120, specifically, in a rotational way for twisting the insertion component retractor 120. The groove 140 may be configured for guiding the movement of the insertion component retractor 120 by restricting a direction of movement of the latch 136. The groove 140 may comprise or may be one or more of a slot, a trench cut and/or an opening of the insertion sleeve 128. The groove 140 may be a trench cut in the insertion sleeve 128 such that the groove 140 may only partially cut into the insertion sleeve 128. Alternatively and/or additionally, the groove 140 may be an opening of the insertion sleeve 128 such that the groove 140 may fully cut the insertion sleeve 128. The groove 140 may extend essentially parallel to the axis of extension 160 of the insertion sleeve 128. Specifically, the groove 140 may extend parallel to the axis of extension 160 and may vary in one or more locations from the direction parallel to the axis of extension 160. For example, the groove 140 may comprise at least one edge 162 and, thus, may diverge from the axis of extension 160 at the location of the edge 162. The edge 162 may be z-shaped edge. Additionally and/or alternatively, the groove 140 may be tilted about an angle with respect to the axis of extension 160.

The cross-sectional view of FIG. 1B shows how the components of the insertion device 110 fit together or interlock. In a center of the insertion device 110 the insertion component retractor 120 is positioned. The insertion component retractor 120 is guided by the insertion sleeve 128 which is surrounded by the inner structure 150 of the cap 122. Within the cap 122, but around the inner structure 150 the guide sleeve 124 is working. The guide sleeve 124 has two ramps 126 which face inward.

In the longitudinal-sectional view of FIG. 1C, it is visualized how the latches 136 of the insertion component retractor 120 work and function together with the insertion sleeve 128 and the inner structure 150 of the cap 122. As outlined above, in FIGS. 1A to 1C the insertion device 110 is shown prior to insertion of the medical device 112. In this position, the latches 136 may be trapped in the z-shaped edge 162 of the insertion sleeve 128. The elastic member 130 pushes from below, but the latches 136 cannot move upwards.

Figure 6:
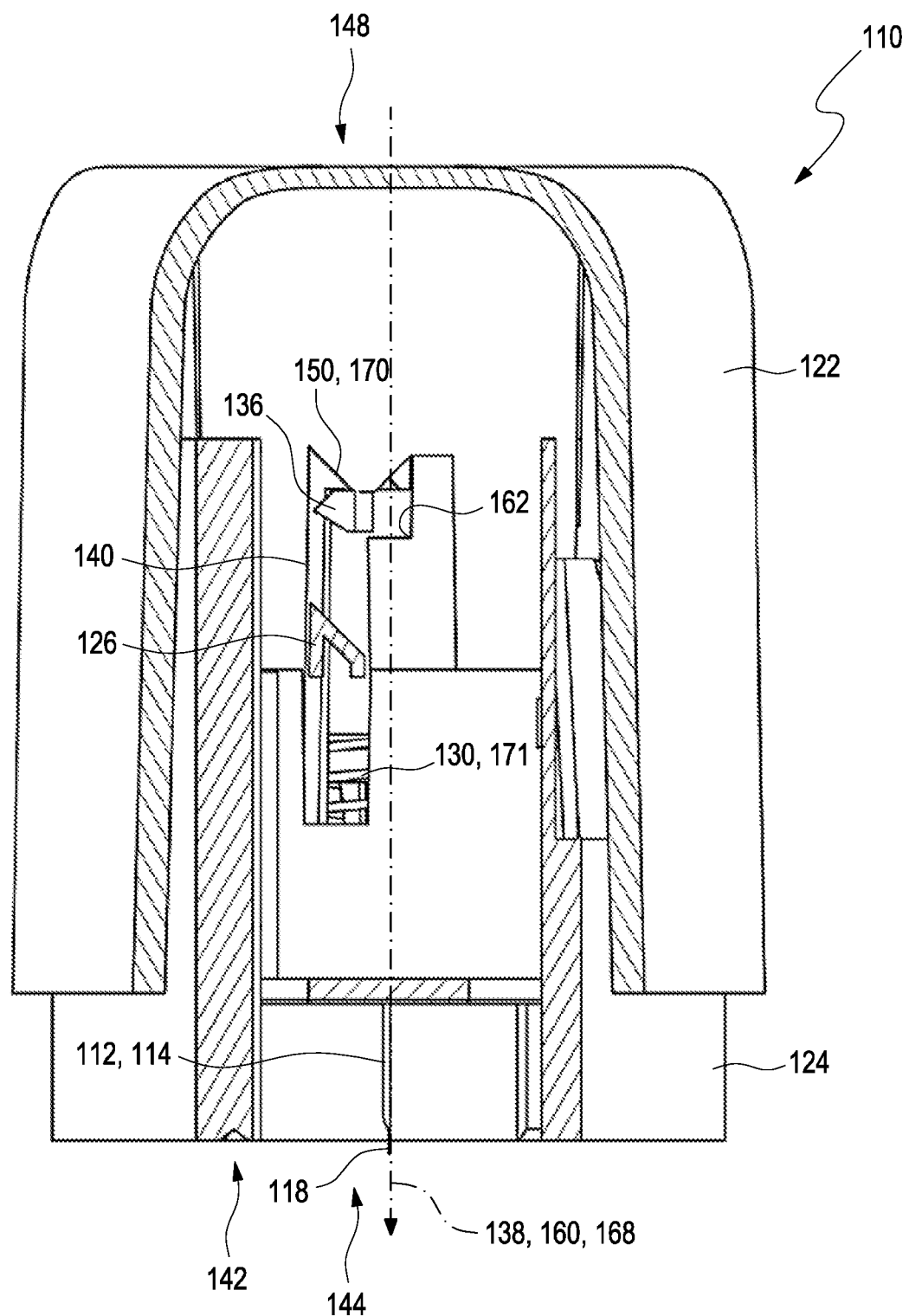
FIGS. 6A to 6C show various longitudinal-sectional views in front of the median plane of the insertion device during insertion of a medical device.
Figure 6:
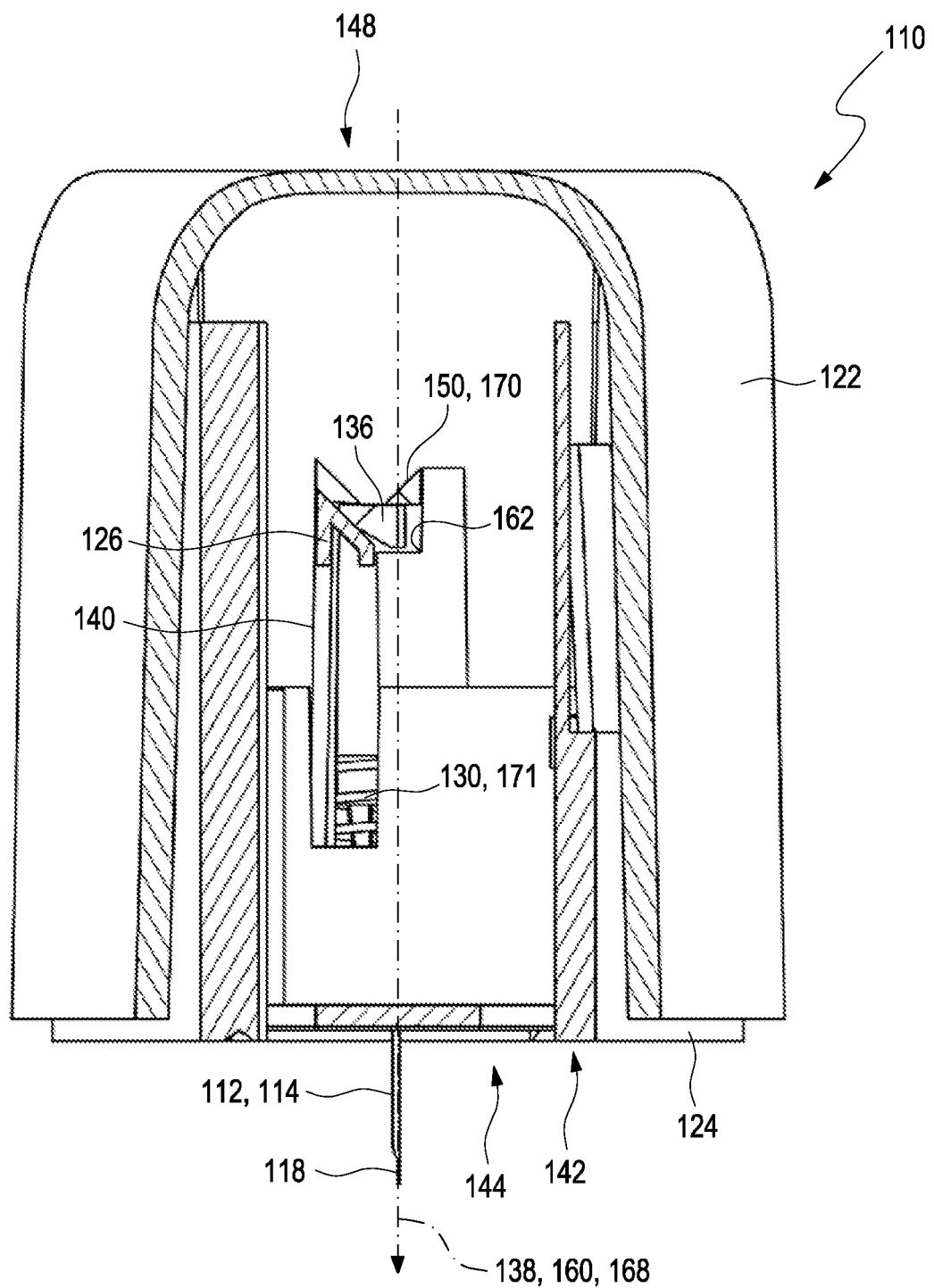
Figure 6:
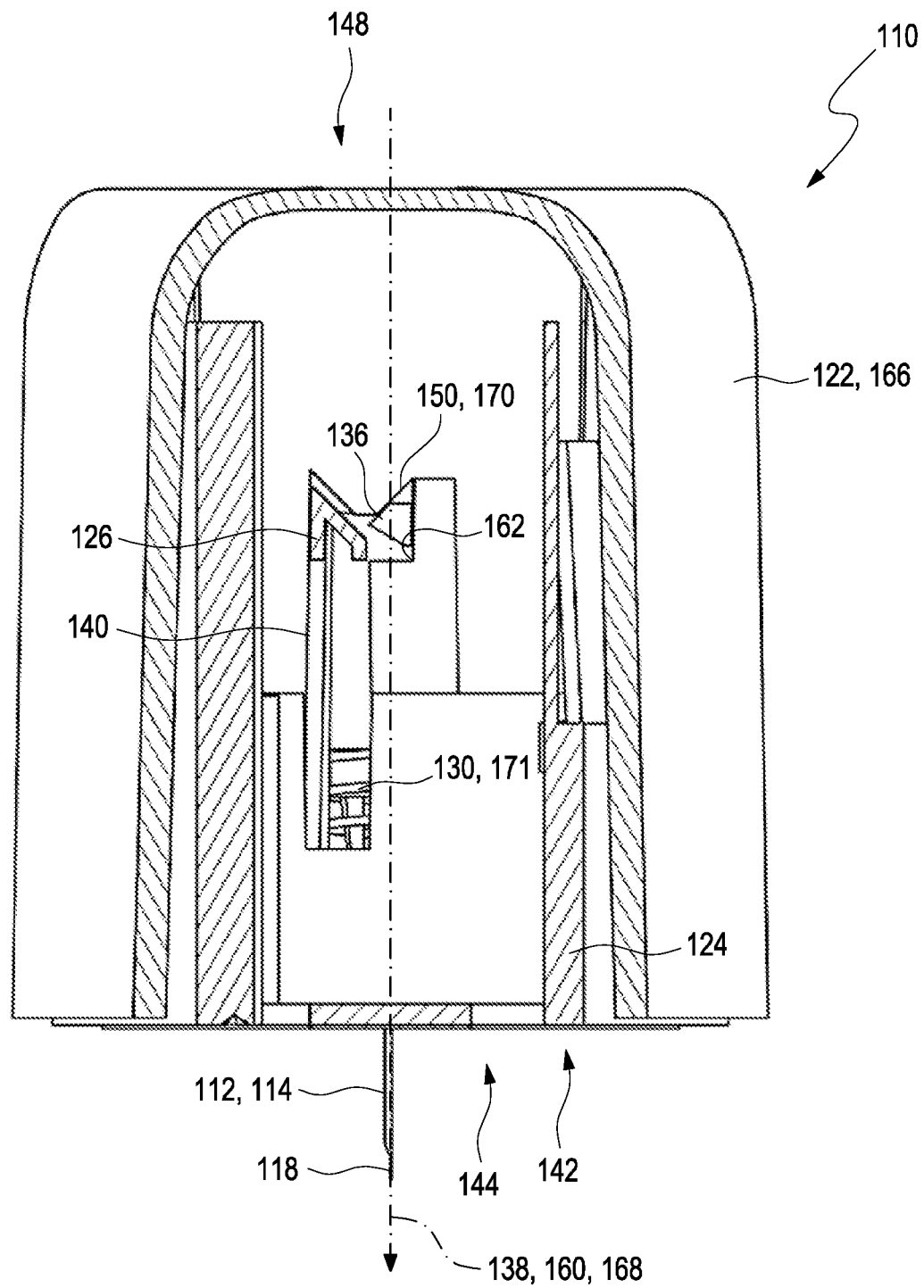

FIGS. 6A to 6C show various longitudinal-sectional views in front of the median plane of the insertion device 110 during insertion of the medical device 112. Specifically, FIGS. 6A to 6C show the insertion movement and retraction movement of the insertion device 110.

For inserting the medical device 112, the cap 122, the insertion component retractor 120 and the insertion sleeve 128 are movable relative to the guide sleeve 124 from a distal position 164 to a proximal position 166. The guide sleeve 124 may be regarded as fix or non-moving component of the insertion device 110 since the guide sleeve 124 is positioned on the user's skin. The other components, such as the medical device 112, the insertion component 118, the insertion component retractor 120, the insertion sleeve 128 and the cap 122 may move in a proximal direction relative to the skin of the user relative to the guide sleeve 124.

The distal position 164 may refer to a position being distanced to the skin site of the user. The distal position 164 may be an initial position prior to the insertion movement of the insertion device 110 and/or any parts thereof. Each component of the insertion device 110 may have its own and/or individual distal position 164. For example, the cap 122, the insertion component retractor 120 and the insertion sleeve 128 may have their own and/or individual distal positions 164, respectively. Prior to insertion, as shown in FIG. 1, the cap 122, the insertion component retractor 120 and the insertion sleeve 128 may be in their distal position 164 and may be ready for inserting the medical device 112 into the body tissue of the user. After insertion, the cap 122 and the insertion component retractor 120 may be moved back to their distal positions 164, respectively, and the insertion component 118 may be retracted from the body tissue when the insertion component retractor 120 may be back in its distal position 164.

The proximal position 166 may be the position of the insertion device 110 and/or any parts thereof in relation to the user in which the insertion component 118 and/or the cap 122 are closest to the proximal side 144 of the insertion device 110. Specifically, for inserting the medical device 112, the insertion device 110 may be brought into contact with the skin site of the user. The proximal position 166 may refer to a position being in close proximity to the skin site of the user. Each component of the insertion device 110 may have its own and/or individual proximal position 166. For example, the cap 122, the insertion component retractor 120 and the insertion sleeve 128 may have their own and/or individual proximal positions 166, respectively. In case the cap 122, the insertion component retractor 120 and the insertion sleeve 128 are in their proximal position 166, the medical device 112 may be inserted into the body tissue of the user. During insertion of the medical device 112, the guide sleeve 124 may be in contact with the skin site of the user and, thus, may be, during insertion, in its proximal position 166.

The movement of the cap 122 together with the insertion component retractor 120 and the insertion sleeve 128 from its distal position 164 to its proximal position 166 may be initiable by an action of the user. Specifically, the action of the user may be or may comprise application of a force to the cap 122 by the user such as by manual pressing and/or pushing the cap 122 downward to the proximal position, in particular to the user's skin.

FIG. 6A shows a beginning of the insertion into the user's skin. The guide sleeve 124 is placed at its proximal end 142 onto the user's skin. The user presses on the cap 122, preferably thereby overcoming an initial force such that the components of the insertion device 110 move together. The ramps 126 approach the latches 126. At the same time the insertion component 118 exits from the guide sleeve 124 and starts to penetrate the skin.

In FIG. 6B, the cap 122, the insertion component retractor 120 and the insertion sleeve 128 are shown close before reaching their proximal position 166. The ramps 126 may be in contact with the latches 136. In this situation, the ramp 126 of the guide sleeve 124 is configured to twist the insertion component retractor 120 relative to the guide sleeve 124 and the insertion sleeve 128.

The twist may be or may comprise a rotational movement of the insertion component retractor 120 with respect to an axis of rotation 168. The twist may be a rotational movement of the insertion component retractor 120 upon itself, e.g., a rotational movement about the axis 168 of rotation being congruent with the axis of extension of the cylindrical body of the insertion component retractor 120. Specifically, the insertion component retractor 120 may be essentially rotationally symmetric and the twist may be a rotational movement about a symmetry axis of the insertion component retractor 120. The twist may be a twist about an angle less than 90°, specifically less than 45°, more specifically less than 15°. Other embodiment are feasible, wherein the twist may be about an angle of more 90° or even more than 180°.

During insertion, movement of the insertion component retractor 120 from its proximal position 166 to its distal position 164 may be prevented by the inner structure 150 of the cap 122 and the force applied by the user on the cap 122. The inner structure 150 may be or may comprise a stopping and/or blocking element 170 configured for receiving the latch 136 of the insertion component retractor 120 and for preventing movement of the insertion component retractor 120 from its proximal position 166 to its distal position 164 during insertion, specifically by blocking movement of the latch 136. In the situation of FIG. 6B, the ramp 126 of the guide sleeve 124 may be configured for forcing the insertion component retractor 120 to twist by guiding the latch 136 to move within the groove 140 of the insertion sleeve 128.

FIG. 6C shows the cap 122, the insertion component retractor 120 and the insertion sleeve 128 in their proximal position 166. The insertion movement may be completed when the cap 122 is in the proximal position 166. The cap 122 when being in the proximal position 166 may align with the proximal end 142 of the guide sleeve 124. In this situation, the ramps 126 may be configured for forcing the latches 136 to move beyond the edge 162 of the groove 140. The elastic member 130 may force the latches 136 and the insertion component retractor 120 to twist further such that the latches 136 may be received by the inner structure 150 of the cap 122. In this situation, the user may still apply the force to the cap 122 such that the elastic member 130 cannot drive the movement of the insertion component retractor 120 from the proximal position 166 to the distal position 164. The insertion component 118 may be able to fully penetrate the skin of the user thereby inserting the medical device 112 into the body tissue of the user.

The movement of the cap 122 together with the insertion component retractor 120 from its proximal position 166 to its distal position 164 may be initiable by relieving the action of the user. Specifically, the user may reduce or may stop applying the force to the cap 122 thereby initiating movement of the cap 122 together with the insertion component retractor 120 from its proximal position 166 to its distal position 164. The elastic member 130 may be configured for driving the insertion component retractor 120 to move from its proximal position 166 to its distal position 164. Specifically, the elastic member 130 may be configured for retracting the insertion component retractor 120 after insertion of the medical device 112. The elastic member 130 may be or may comprise at least one spring 171. The spring 171 may be connected to the insertion component retractor 120. The spring 171 may be pre-tensioned, specifically in between the insertion sleeve 128 and the insertion component retractor 120. Provided that the user applies the force to the cap 122, the spring 171 may not be able to move the insertion component retractor 120 and the cap 122 from their proximal position 166 to their distal position 164, respectively. The spring 171 may be actuable by releasing a force applied to the cap 122.

As outlined above, the insertion device 110 may comprise the at least one plunger 119 fixedly connected to the insertion component 118. The insertion component retractor 120 may be connected to the plunger 119. The insertion component retractor 120 may be configured for engaging with the plunger 119 when being moved from its proximal position 166 to its distal position 164. Specifically, the insertion component retractor 120 may engage with the plunger 119 by using the grippers 132. During retraction, the insertion component retractor 120 may be moved from its proximal position 166 to its distal position 164 thereby engaging to the plunger 119 such that the plunger 119 may be moved together with the insertion component 120 fixedly engaged with the plunger 119 from the proximal 166 to the distal position 164. Thus, the insertion component 118 may be retracted by the movement of the insertion component retractor 120 from its proximal position 166 to its distal position 164.

A short time delay of at least 100 ms may occur after insertion and before the retraction of the insertion component 118 starts. In particular, when the insertion device 110 is applied to the skin site of the user, the skin typically bulges towards the interior of the insertion device 110. The short time delay between the insertion device 110, in particular the insertion component 118, being in the proximal position 166 and the insertion device 110, in particular the insertion component 118, being moved back in its distal position 164 allows application of pressure onto the bulged skin. Thereby sliding of the insertion component 118 together with the medical device 112 into the skin is facilitated and enables the skin of the user to slide over the entire length of the insertion component 118 and the medical device 112.

Figure 7:
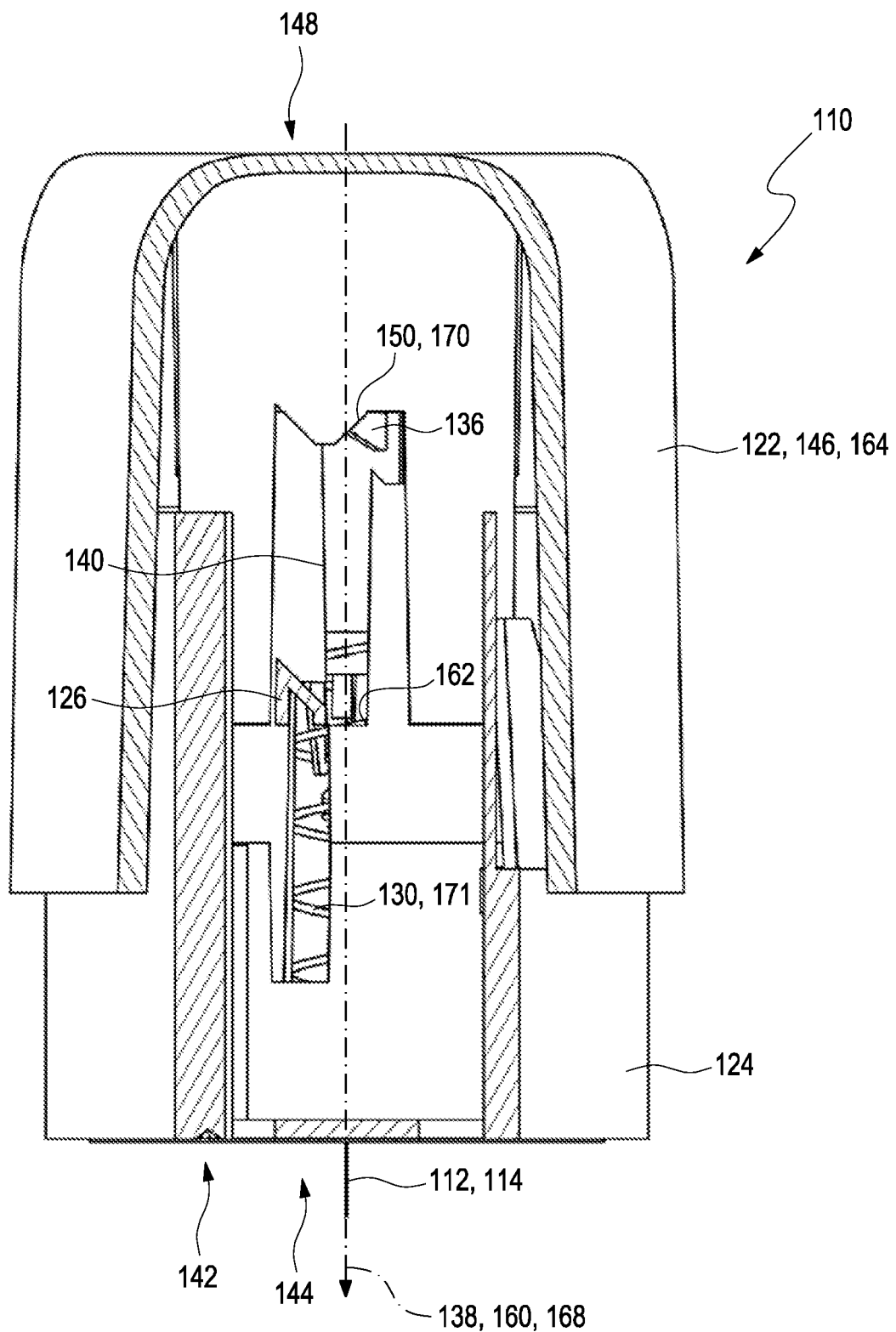
FIGS. 7A to 7C show longitudinal-sectional views in front of the median plane and in the median plane of the insertion device after retraction of an insertion component.
Figure 7:
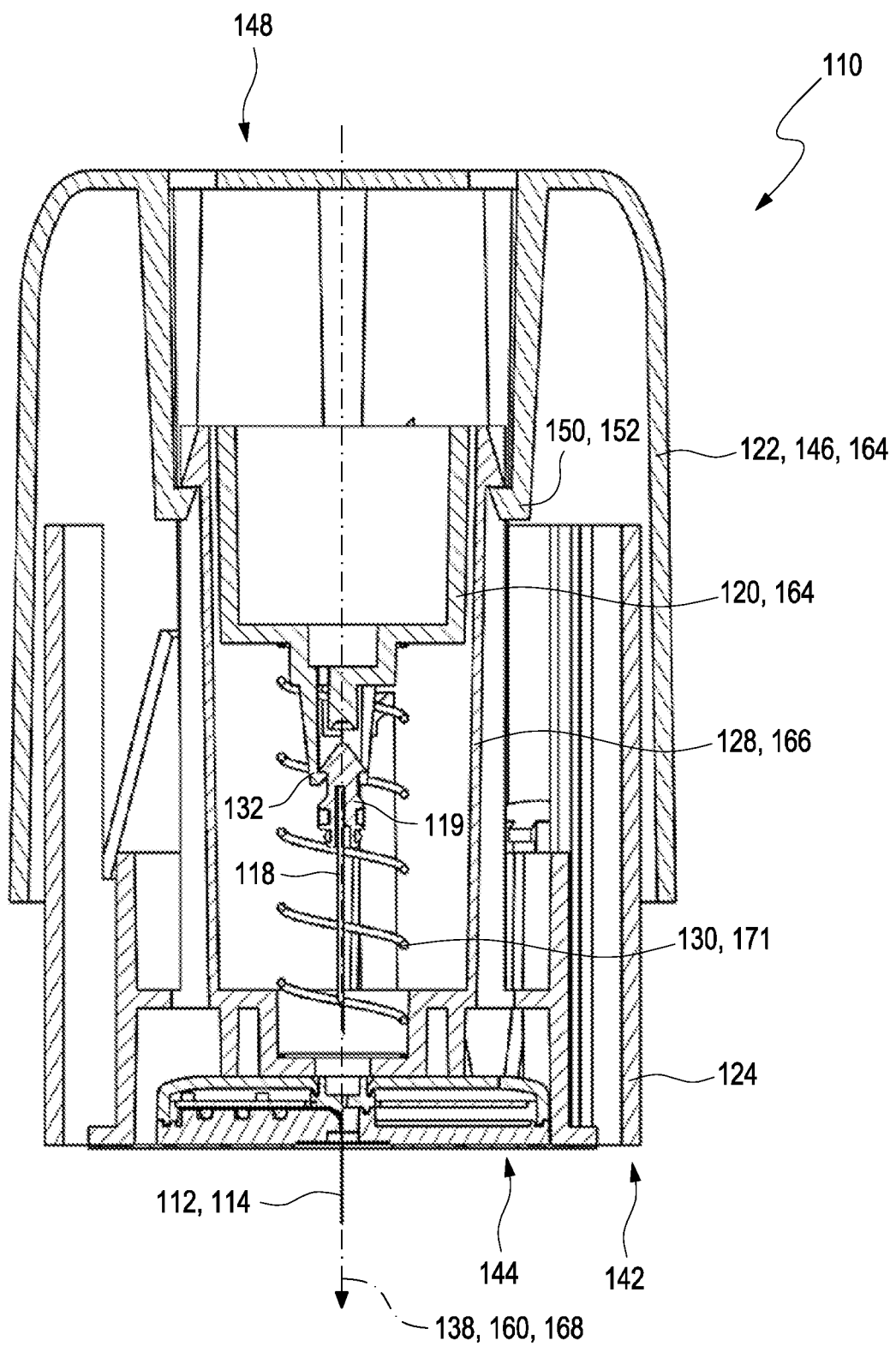
Figure 7:
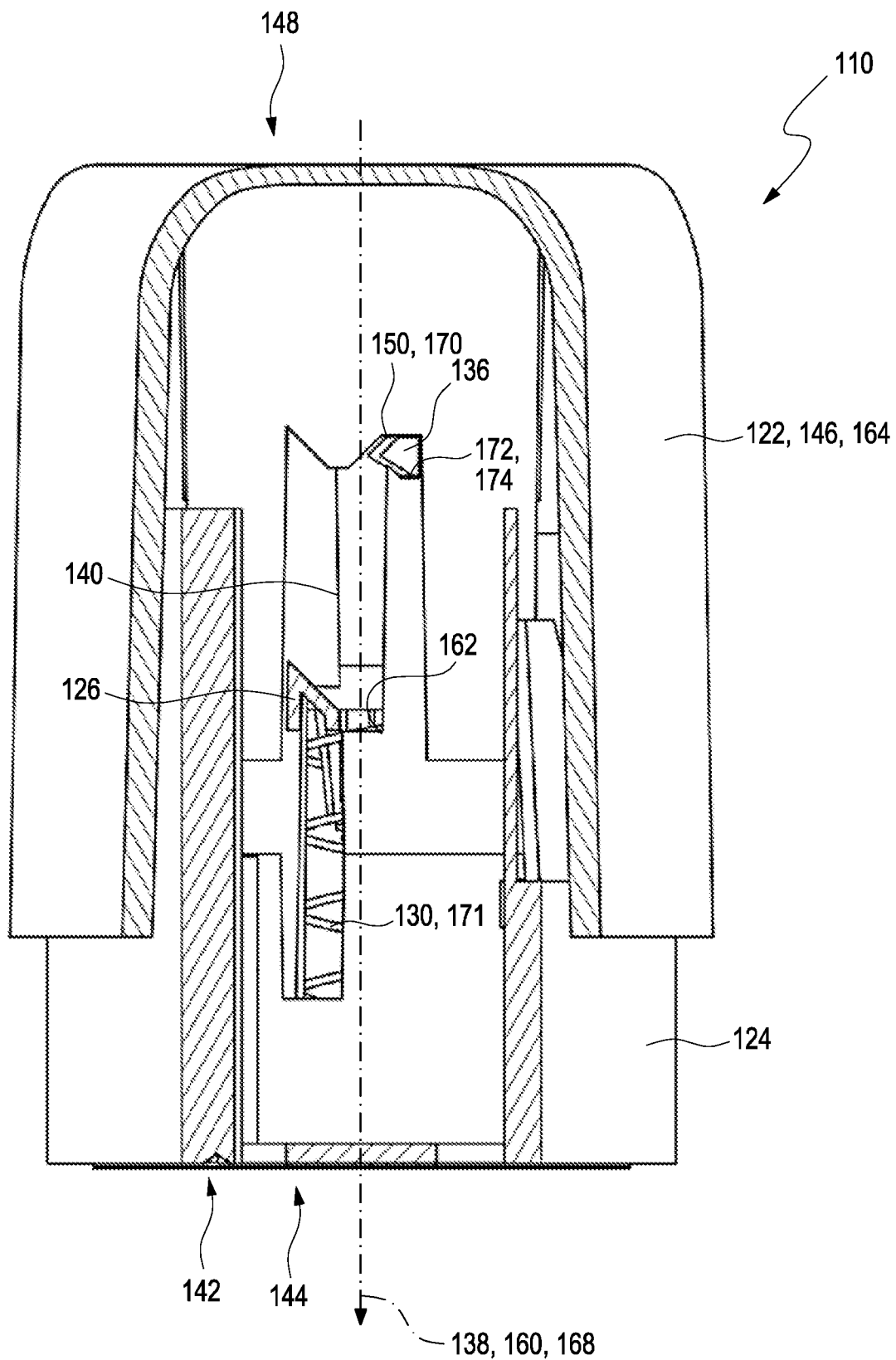

FIGS. 7A to 7C, show longitudinal-sectional views in front of the median plane of the insertion device 110 after retraction of the insertion component 118, i.e., back in the distal position 164.

As shown in FIG. 7A, in the distal position 164, the latch 136 may be released from the groove 140 and the insertion component retractor 120 may twist to be received by the inner structure 150 of the cap 122. The insertion component 118 may be fully retracted from the body tissue. FIG. 7B shows functioning of the latching elements 152 which have interlocked the cap 122 with the other components of the insertion device 110.

The insertion device 110 may further comprise at least one safety lock 172, as shown in FIG. 7C. The safety lock 172 may be configured for preventing removement, in particular reuse, of the insertion device 110, in particular after insertion of the medical device 112 and retraction of the insertion component 118. The safety lock 172 may be configured for preventing an unwanted re-actuation of the insertion device 110. The safety lock 172 may be configured for locking the insertion device 110, wherein in the locked insertion device 110 an unwanted reuse may be prevented.

The safety lock 172 may comprise one or more components being mounted at different components of the insertion device 110. For example, the at least one safety notch 174 may be arranged at the insertion sleeve 128 and being configured for receiving the latch 136 of the insertion component retractor 120. The safety notch 174 may be arranged adjacent to the groove 140 of the insertion sleeve 128 such that the latch 136 may be received in the safety notch 174 when the groove 140 guides the latch 136 and the insertion component retractor 120 from its proximal position 166 to its distal position 164. The latch 136 may be received by the safety notch 174 such that removement thereof may be prevented. Specifically, the safety notch 174 may block removement of the latch 136 and the insertion component retractor 120 when the user applies a force to the cap 122 once more. Thus, the risk of unintentional injuries may be minimized.

As seen, for example, in FIG. 1A, the insertion device 110 may further be configured for receiving a sensor patch 176 and for attaching the sensor patch 176 to the skin site of the user. The insertion device 110 may be configured for attaching and/or arranging the sensor patch 176 to the skin site of the user, in particular simultaneously with the insertion of the insertion component 118 into the body tissue of the user. The sensor patch 176 may comprise the electronics unit 116 which may be configured for being connected to the medical device 112, specifically to the analyte sensor 114. The sensor patch 176 may comprise at least one adhesive means for being attached to the skin site of the user such as plaster or the like. The sensor patch 176 may remain attached to the skin site of the user after the medical device 112 was inserted into the body tissue of the user. The insertion component 118 may protrude through the sensor patch 176 received by the insertion device 110. The insertion component retractor 120 may be configured for grabbing the insertion component 118 in the sensor patch 176 prior to insertion of the medical device 112.

Figure 8:
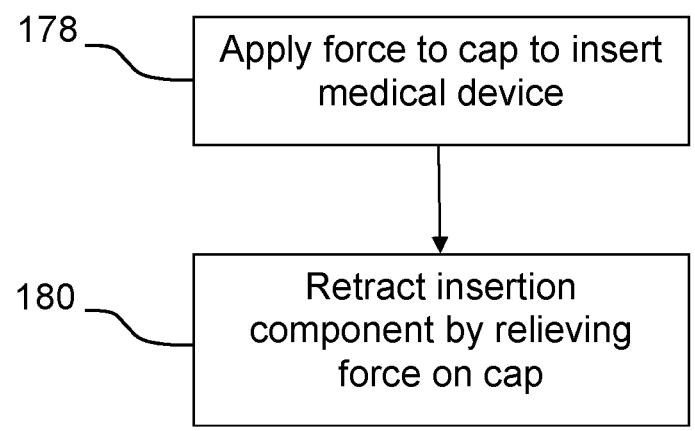
FIG. 8 shows a flow chart of an embodiment of a method for inserting a medical device into a body tissue of a user.

FIG. 8 shows a flow chart of an exemplary embodiment of a method for inserting the medical device 112 into the body tissue of the user. The method comprises using the insertion device 110 according to this disclosure, such as according to any one of the embodiments disclosed above and/or any one of the embodiments disclosed in further detail below. Thus, reference may be made to the description of FIGS. 1 to 7C. The method comprises the following steps which specifically may be performed in the given order. The method may comprise further steps which are not listed.

The method comprises:
- a) (denoted by reference number 178) inserting the medical device 112 into the body tissue of the user by applying the force on the cap 122 of the insertion device 110 thereby moving the insertion component 118, the cap 122, the insertion component retractor 120 and the insertion sleeve 128 relative to the guide sleeve 124 from the distal position 164 to the proximal position 166; and
- b) (denoted by reference number 180) retracting the insertion component 118 by relieving the force applied to the cap 122 thereby moving the cap 122 from its proximal position 166 to its distal position 164, thereby moving the insertion component retractor 120 from its proximal position 166 to its distal position 164.

The movement of the cap 122 together with the insertion component retractor 120 and the insertion sleeve 128 from its distal position 164 to its proximal position 166 may be initiated by action of the user, specifically by applying the force to the cap 122 of the insertion device 110. The force may be applied by the user of the insertion device 110 before and during the insertion of the medical device 112. The insertion of the medical device 112 may be started by setting the guide sleeve 124, in particular the proximal end 142 of the guide sleeve 124, in contact with the skin of the user, specifically at an insertion site. Thus, step a) of the method may comprise applying the insertion device 110 to the skin site of the user, in particular applying the guide sleeve 124 of the insertion device 110 to the skin site of the user.

Prior to insertion, the insertion sleeve 128 may be in its distal position 164 and may be at least partially enclosed by the guide sleeve 124 in its distal position 164. The cap 122 may be in contact to the insertion sleeve 128, specifically at the distal end 156 of the insertion sleeve 128. Prior to insertion, the insertion component retractor 120 may be in its starting position and may be at least partially enclosed by the insertion sleeve 128. The elastic member 130 may be in between the insertion component retractor 120 and the insertion sleeve 128 and may be at full tension. The insertion component retractor 120 may be locked in this position by the at least one latch 136 which may be received by the edge 162 in the groove 140 of the insertion sleeve 128.

When the user exerts the force to the cap 122, the arm of the user, which applies the force to the cap 122, may accelerate in proximal direction, specifically towards the skin of the user. Shortly before the insertion sleeve 128 reaches its proximal position 166, the latch 136 of the insertion component retractor 120 may get in contact with the at least one ramp 126 of the guide sleeve 124, wherein the ramp 126 may specifically protrude inwardly the guide sleeve 124. The insertion component retractor 120 may be twisted by the interaction of the ramp 126 and the latch 136. The latch 136 may fall loose from the edge 162 in the groove 140 of the insertion sleeve 128 and may get in contact to the inner structure 150 of the cap 122. The arm of the user may get stopped by the contact between the insertion sleeve 128, in particular the sensor patch 176 which is in an embodiment comprised in the insertion device, and the skin of the user. Because of the kinetic energy of the mass of the arm, this stopping may cause pressure of the insertion sleeve 128, in particular the sensor patch 176 which is in an embodiment comprised in the insertion device, against the skin of the user.

Step b) may comprise relieving the force applied to the cap 122. Triggered by relieving the force applied to the cap 122, the insertion component 118 may be moved back from the skin site of the user. When the user releases the force, the spring 171 may force the insertion component retractor 120 and in consequence the cap 122 into movement to the distal position 164. The latch 136 may slide along the groove 140 in the insertion sleeve 128 until the insertion component 118 may be totally retracted from the body tissue of the user. The latch 136 may be forced by the inner structure 150 of the cap 122 and the spring 171 may force to twist the insertion component retractor 120 even further into a position where the latch 136 may not be able to move any further, specifically into a position where the insertion component retractor 120 cannot move in proximal direction any more. The insertion component retractor 120 cannot move in proximal direction any more since the latch 136 may be received by the safety lock 172, more specifically by the safety notch 174 of the insertion sleeve 128. Thus, after insertion of the medical device 112, the insertion component 118 may be safely locked by the safety lock 172 of the insertion device 110.

The insertion device 110 according to this disclosure may change the order of movements compared to know insertion devices. In known insertion devices the insertion component may exert a force to the skin in which the medical device shall be inserted. The skin bulges inwardly under this force. In known insertion devices near the end of the insertion movement the insertion component is retracted. Because of the inward bulging of the skin and the indenting of the skin under the attack of the insertion component 118, the medical device, however, may not fully be inserted when the insertion component starts to disappear rapidly. Thus, the result may be a not or just partly inserted medical device. The insertion device 110 according to this disclosure compensates the indenting of the skin by applying pressure, in particular with the sensor patch 176 to the skin while the insertion element 118 still protrudes in its full length from the insertion device 110 into the skin. This may ensure a reliable insertion of the medical device 112 into the body tissue of the user. After this, the insertion component 118 may be retracted.

Figure 9:
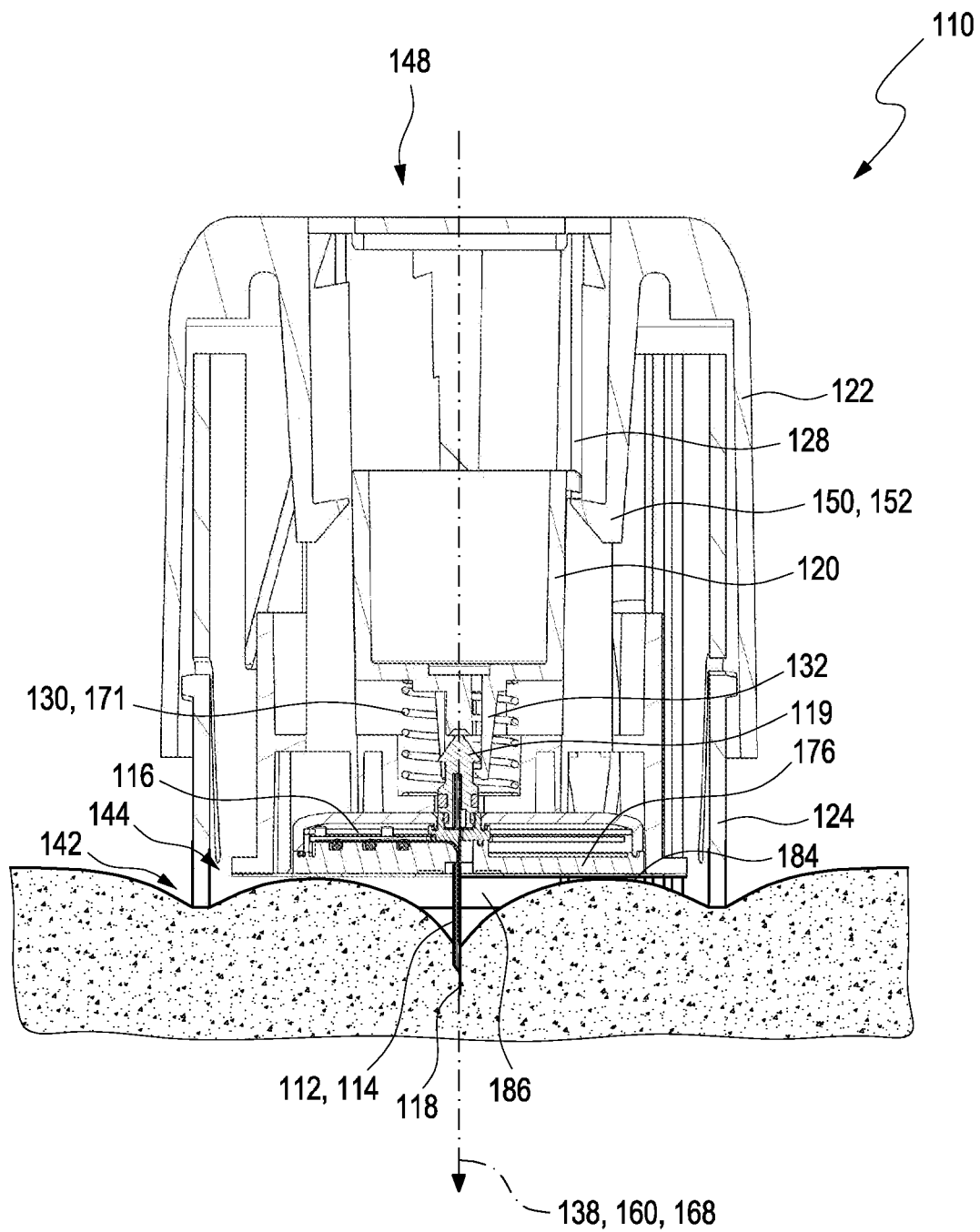
FIGS. 9A and 9B show longitudinal-sectional views in the median plane of the insertion device during insertion of a medical device.
Figure 9:
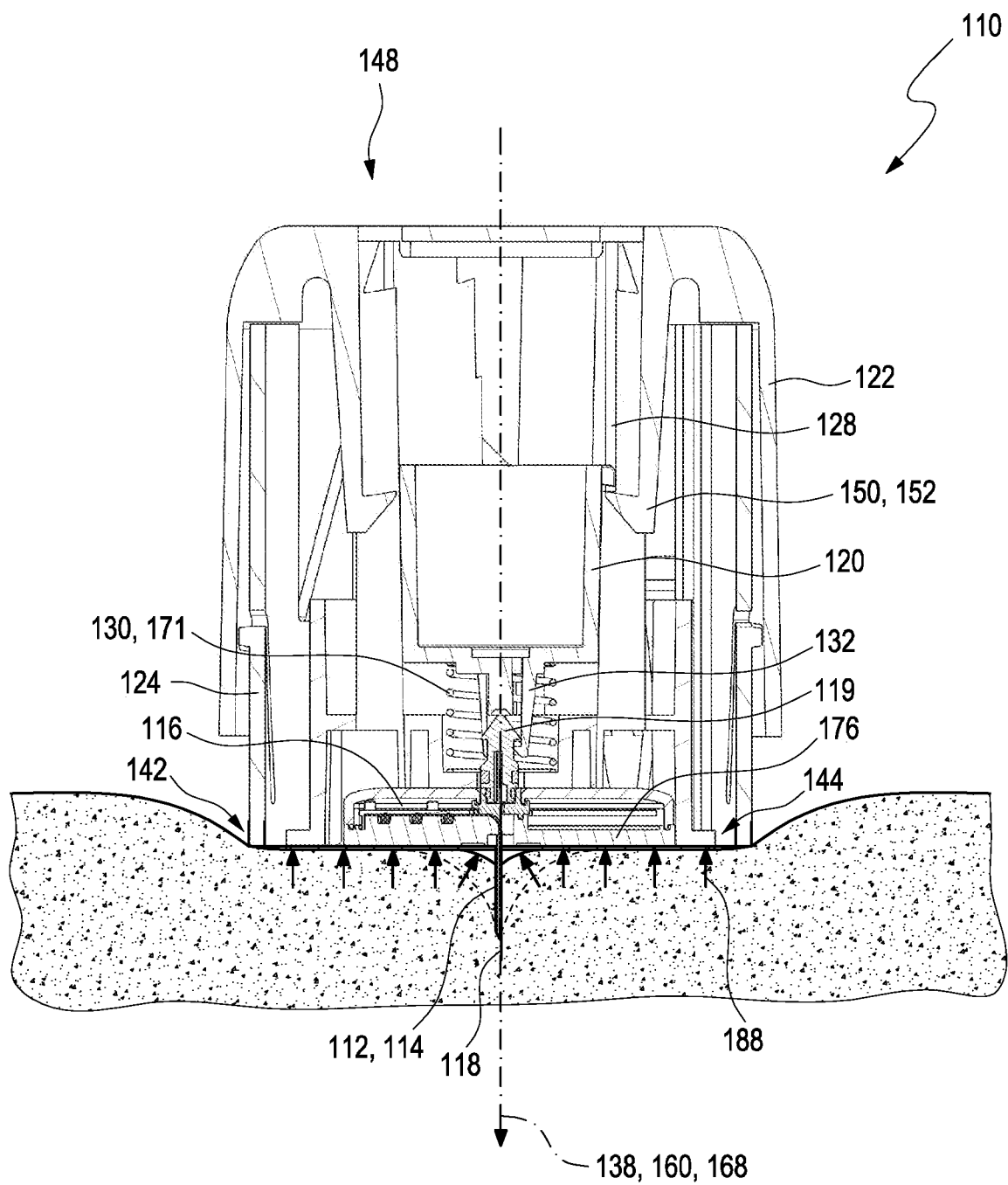

FIGS. 9A and 9B visualize the effect of application of pressure onto the bulged skin by the sensor patch 176, specifically allowing compensating of the inward bulging of the skin. FIGS. 9A and 9B show longitudinal-sectional views in the median plane of the insertion device 110 during insertion of the medical device 112. With respect to a description of the insertion device 110 shown in FIGS. 9A and 9B reference is made to the description of FIGS. 1 to 7C. In the exemplary embodiment shown in FIGS. 9A and 9B, the insertion device 110 comprises the sensor patch 176.

In FIG. 9A, the insertion device 110 is shown during insertion of the medical device 112 when the insertion component 118 starts to penetrate the skin of the user. When the insertion device 110, specifically the proximal end 142 of the guide sleeve 124, is applied to the skin of the user, the skin typically bulges toward the interior of the insertion device 110. The bulging of the skin is indicated in FIG. 9A by reference number 184. The penetration of the insertion component 118 through the skin of the user may cause an indentation of the skin, as it is indicted in FIG. 9A by reference number 186. During insertion of the medical device 112, the sensor patch 176 may be pressed against the skin of the user before the cap 122, the insertion component retractor 120 and the insertion sleeve 128 reach their proximal position 166, see FIG. 9B. The short time delay between the insertion device 110, in particular the insertion component 118, being in the proximal position 166 and the insertion device 110, in particular the insertion component 118, being moved back in its distal position 164 allows application of pressure onto the bulged skin by the sensor patch 176, indicated with arrows 188. This pressure allows for compensating the inward bulging of the skin as well as the indenting of the inward bulged skin by the insertion component 118. Thus, the sliding of the insertion component 118 together with the medical device 112 into the skin is facilitated, as described above.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS 110 insertion device
112 medical device
114 analyte sensor
116 electronics unit
118 insertion component
119 Plunger
120 insertion component retractor
122 Cap
124 guide sleeve
126 Ramp
128 insertion sleeve
130 elastic member
132 Gripper
134 proximal end of the insertion component retractor
136 Latch
138 insertion direction
140 Groove
142 proximal end of the guide sleeve
144 proximal side of the insertion device
146 proximal position of the cap
148 distal side of the insertion device
150 inner structure
152 latching element
154 Receptacle
155 receptacle for the medical device
156 distal end of the insertion sleeve
158 proximal end of the insertion sleeve
160 axis of extension
162 Edge
164 distal position
166 proximal position
168 axis of rotation
170 blocking element
171 Spring
172 safety lock
174 safety notch
176 sensor patch
178 inserting the medical device
180 retracting the insertion component
182 Opening
184 bulging of the skin
186 indentation of the skin
188 Pressure

What is claimed is:

1. An insertion device, comprising:
   i) a medical device;
   ii) an insertion component configured for inserting the medical device into body tissue of a user;
   iii) an insertion component retractor;
   iv) a cap;
   v) a guide sleeve comprising a ramp;
   vi) an insertion sleeve; and
   vii) an elastic member;
   wherein, for inserting the medical device, the cap, the insertion component retractor and the insertion sleeve are movable relative to the guide sleeve from a distal position to a proximal position, wherein the ramp is configured to twist the insertion component retractor relative to the guide sleeve and the insertion sleeve when the cap is moved from its distal position to its proximal position, wherein the cap is movable from its proximal position to its distal position and the insertion component retractor is thereby moved from its proximal position to its distal position.

2. The insertion device according to claim 1, wherein the movement of the cap together with the insertion component retractor and the insertion sleeve from its distal position to its proximal position is initiable by an action of the user.

3. The insertion device according to claim 1, wherein the movement of the cap together with the insertion component retractor from its proximal position to its distal position is initiable by relieving the action of the user.

4. The insertion device according to claim 1, wherein before reaching the proximal position of the insertion component retractor, the ramp contacts a latch of the insertion component retractor and the ramp twists the latch and thereby twists the insertion component retractor.

5. The insertion device according to claim 4, wherein the insertion sleeve comprises a groove configured for guiding the latch, wherein the groove comprises at least one edge.

6. The insertion device according to claim 5, wherein the ramp is configured for forcing the insertion component retractor to twist by guiding the latch to move within the groove.

7. The insertion device according to claim 1, wherein the elastic member is configured for driving the insertion component retractor from its proximal position to its distal position, wherein the elastic member comprises a spring connected to the insertion component retractor, wherein the spring is pre-tensioned and is actuatable by releasing a force applied to the cap.

8. The insertion device according to claim 7, wherein the spring is configured to drive the insertion component retractor from its proximal position to its distal position and thereby drive the cap from its proximal position to its distal position.

9. The insertion device according to claim 1, wherein the cap when in the proximal position aligns with a proximal end of the guide sleeve.

10. The insertion device according to claim 1, further comprising a safety lock configured for preventing re-movement of the insertion component retractor after being moved to its distal position.

11. The insertion device according to claim 1, further comprising an analyte sensor for detecting at least one analyte in a body fluid of a user.

12. The insertion device according to claim 11, wherein the analyte sensor has two-electrodes.

13. A method for inserting a medical device into a body tissue of a user using an insertion device according to claim 1, comprising:
  a) inserting the medical device into the body tissue of the user by applying a force on the cap of the insertion device, thereby moving the insertion component, the cap, the insertion component retractor and the insertion sleeve relative to the guide sleeve from a distal position to a proximal position, and twisting the insertion component retractor relative to the guide sleeve and the insertion sleeve; and
  b) retracting the insertion component by relieving the force applied to the cap thereby moving the cap from its proximal position to its distal position, thereby moving the insertion component retractor from its proximal position to its distal position.

14. The method according to claim 13, further comprising bringing the proximal end of the guide sleeve in contact with a skin site of a user and applying pressure to the skin site of the user with the sensor patch.

15. The method according to claim 13, wherein the movement of the cap together with the insertion component retractor and the insertion sleeve from its distal position to its proximal position is initiated by action of the user.

16. The method according to claim 13, wherein the movement of the cap together with the insertion component retractor from its proximal position to its distal position is initiated by relieving action of the user.

* * * * *